(12) United States Patent
Miculka et al.

(10) Patent No.: US 6,699,978 B1
(45) Date of Patent: Mar. 2, 2004

(54) LINKER NUCLEOSIDE, AND PRODUCTION AND USE OF THE SAME

(75) Inventors: Christian Miculka, Frankfurt (DE); Norbert Windhab, Hattersheim (DE); Tilmann Brandstetter, München (DE); Stefan Scherer, Büttelborn (DE)

(73) Assignee: Nanogen Recognomics GmbH, Frankfurt (DE)

( * ) Notice: Subject to any disclaimer, the term of this patent is extended or adjusted under 35 U.S.C. 154(b) by 0 days.

(21) Appl. No.: 09/509,011

(22) PCT Filed: Sep. 21, 1998

(86) PCT No.: PCT/EP98/06000

§ 371 (c)(1), (2), (4) Date: Jul. 11, 2000

(87) PCT Pub. No.: WO99/15542

PCT Pub. Date: Apr. 1, 1999

(30) Foreign Application Priority Data

Sep. 22, 1997 (DE) .......................... 197 41 738

(51) Int. Cl.$^7$ .......................... C07H 19/00; C07H 21/00
(52) U.S. Cl. .................. 536/22.1; 536/23.1; 536/26.7; 536/26.8; 536/27.13; 536/27.21; 536/27.6; 536/27.8; 536/28.53; 536/28.54; 536/28.55
(58) Field of Search .............................. 536/22.1, 23.1, 536/26.7, 26.8, 27.13, 27.21, 27.6, 27.8, 27.81, 28.5, 28.53, 28.54, 28.55

(56) References Cited

U.S. PATENT DOCUMENTS

| 5,391,723 A | 2/1995 | Priest |
| 5,624,802 A | 4/1997 | Urdea et al. |
| 5,632,957 A | 5/1997 | Heller et al. |

FOREIGN PATENT DOCUMENTS

| DE | 2028906 | | 12/1970 |
| EP | 0057548 | | 8/1982 |
| WO | WO 89/02439 | | 3/1989 |
| WO | WO 94/28173 | | 12/1994 |
| WO | WO 96/13522 | | 5/1996 |
| WO | WO 96/13613 | | 5/1996 |
| WO | WO 97/05156 A | | 2/1997 |
| WO | WO 97/12896 A | | 4/1997 |
| WO | WO 97/28176 | | 8/1997 |
| WO | WO 97/28176 A | | 8/1997 |
| WO | WO99/52923 | * | 10/1999 |
| WO | WO 93/20242 | | 10/2000 |

OTHER PUBLICATIONS

Hayakaway, Y. et al, O–Allyl Protection of Guanine and Tymine Residues in Oligodeoxyribonucleotides:, vol. 58, No. 20 (1993), pp. 5551–5555, also referred to as XP 002094188.

DeClerq et al., "Antiviral Activity of Novel Deoxyuridine Derivatives", vol. 1 (Sep. 1977) pp. 352–355, also referred to as XP 002094189.

Eschenmoser et al, "147. Why Pentose–and Not Hexose–Nucleic Acids?", vol. 76, (1993), pp. 2161–2183, also referred to as 002094190.

Hanna, M., "Photochemical Cross–Linking Analysis of Protein–Nucleic Acid Interactions in *Escherichia Coli* Transcription Complexes from Lambda $P_R$ Promoter", vol. 274, (1996), pp. 403–418, also referred to as XP 002045925.

Pitsch, et al, Helv. Chim. Acta. 1993, vol. 76, "Why Pentose and Not Hexose–Nucleic Acids?" pp. 2161–2183.

Pitsch, et al, Helv. Chim. Acta. 1995, vol. 78, "Pyranosyl RNA (p–RNA): Base–Pairing Selectivity and Potential to Replicate", pp. 1621–1635.

Vorbrüggen, et al, Chem. Ber. 1981, "Nucleoside Synthesis with Trimethylsilyl Triflate and Perchlorate as Catalysts", pp. 1234–1255.

Suvorov N.N. et al, Biol. Aktivn, Soedin., Akad, Nauk SSSR 1965, 60.

Tetrahedron, 1967, vol. 23, "Stabitlity and Equilibria of Free Radicals–III", pp. 4661–4673.

Dobriynin Y.V. et al, Khim–Farm. Zh. 1978, 12, 33.

Nelson, et al, Nucleic Acids Research, vol. 17, No. 18, 1989, pp. 7170–7179.

Noyori et al, J. Am Chem. Soc. 1990, 112, pp. 1691–1696.

Letsinger et al, Nature, vol. 382, 1996, "A DNA–Based Method for Rationally Assembling Nano–Particles into Macroscopic Materials", pp. 607–609.

Schultz et al, Narute, vol. 382, 1996, "Organization of 'Nanocrystal Molecules' Using DNA", pp. 609–611.

Lombardi et al, 1997, 40, "DeNovo Design of Heterotrimeric Coliled Coils", pp. 495–504.

Skerra and Plückthun, Science, vol. 240, 1998, "Assembly of a Functional Immunoglobin Fv Fragment in *Escherichia Coli*" pp. 1038–1041.

Bird, et al, Science vol. 242, 1988, "Single–Chain Antigen–Binding Proteins", pp. 423.

Huston et al, 1988, Proc. Natl. Acad. Sci. U.S.A., 85, pp. 5879–5883, "Protein Engineering of Antibody Binding Sites: Recovery of Specific Activity in an Anti–dioxin Single–Chain Fv Analogue Produced in *Escherichia Coli*".

Better et al, 1988, Science vol. 240, "*Escherichia Coli*' Secretion of Active Chimeric Antibody Fragment", pp. 1041–1043.

(List continued on next page.)

*Primary Examiner*—James O. Wilson
*Assistant Examiner*—Patrick Lewis
(74) *Attorney, Agent, or Firm*—O'Melveny & Myers LLP

(57) ABSTRACT

The present invention relates to a linker nucleoside, its preparation and use for the covalent bonding of biomolecules to oligonucleotides, in particular p-RNA oligonucleotides.

54 Claims, 4 Drawing Sheets

OTHER PUBLICATIONS

Urdea, Boi/Technology 1994, vol. 12, "Branched DNA Signal Amplification", pp. 926–928.

Mullis K, "Methods Enzymol", 1987, 155, 335.

Zhu et al, Bioconjugate Chem. 1994, 5, "Preparation of Vitamin B6–Conjugated Peptides at the Amino Terminus and of Vitamin B6 Peptide–Oligonucleotide Conjugates", pp. 312–315.

Foder et al, Nature, vol. 364, 1993, "Multiplexed Biochemical Assays with Biological Chips", pp. 555–556.

Southern et al, Genomics 13 , 1992, "Analyzing and Comparing Nucleic Acid Sequences by Hybidization to Arrays of Oligonucleotides: Evaluation Using Experimental Models", pp. 1008–1017.

Kuehne et al, J. Org. Chem. Vol. 43, No. 13, 1978, Communications, pp. 2733–2735.

Gait, M.J., "Oligonucleotide Synthesis", IRL Press, Oxford, UK 1984.

Fissekis, et al, J. Org. Chem. 1964, vol. 29, "Synthesis of 5–Hydroxyalkylpyrimidines From Lactones".

Fissekis, et al, J. Org. Chem. vol. 28, No. 2, 1973, "The Chemistry of some 5–(2–Hydroxyalkyl) Uracil Derivatives and a Synthesis of 5–Vinyluracil", pp. 264–269.

Aketa et al, Chem.Pharm Bull, 1976, 24, 621.

Nelson, P.S. et al. "Oligonucleotide labeling methods 3. Direct labeling of oligonucleotides employing a novel, non–nucleoside, 2–aminobutyl–1,3–propanediol backbone." Nucleic Acids Research 20 (23):6253–59 (1992).

Tabone, John C., et al. "Factors influencing the extent and regiospecificity of cross–link formation between single–stranded DNA and reactive complementary oligodeoxynucleotides." Biochemistry 33(1):375–83 (1994).

Uddin, Andre H., et al. "A novel N3–functionalized thymadine linker for the stabilization of triple helical DNA." Chemical Communications 2:171–2 (1996).

Adams, David R., et al. "Preparation and Anti–HIV acitivity of N–3–Substituted Thymidine Nucleoside Analogs." J. MED. CHEM. 40: 1550–58 (1997).

Cadet, J. Tetrahedron Letters 11: 867–70 (1974).

De Clercq, E., et al. "Ref. 132049y: Effects of E–5–(2–bromovinyl)–2'–deoxyuridine and other selective antiherpes compounds on the Induction of retrovirus particles in mouse BALB/373 cells." CHEMICAL ABSTRACTS 94: 36 (1981).

Doboszewski, B., et al. "3'–Deoxy–3'–Hydroxymethyl–aldopentopyranosyl Nucleoside Synthesis. Part I." Tetrahedron 51(18): 5381–96 (1995).

Edwards, Christine, et al. "Synthesis of 2–substituted 2'–deoxyguanosines and 6–O–allylguanines via activation of C–2 by a trifluoromethanesulfonate group." J. Chem. Soc., Perkins Trans. 1: 1887–93 (1997).

Gibson, Katharine J., et al. "Ref. 71626t: Synthesis and Application of derivatizable Oligonucleotides." Chemical Abstracts 108 (1988).

Gibson, Katharine J., et al. "Synthesis and application of derivatizable oligonucleotides." Nucleic Acids Research 15(16): 6455–67 (1987).

Gupta, Vineet et al. "A Self–Cleaving DNA Nucleoside." Chem. Commun. 1425–26 (1997).

Holy, A. "Preparation of Acyl Derivatives of Pyrimidin–2–one Nucleosides by the Silyl Variant of the Hilbert–Johnson Reaction." Collection Czechoslov. Chem. Commun. 42: 902–08 (1977).

Hossain, Nafizal, et al. "Synthesis and Antiviral Activity of the $\alpha$–Analogues of 1,5–Anhydrohexitol Nucleosides (1,5–Anhydro–2,3–dideoxy–D–ribohexitol Nucleosides)." J. Org. Chem.. 62: 2442–47 (1997).

Iyer, Radhakrishnan P., et al. "N–pent–4–enoyl (PNT) Group as a Universal Nucleobase Protector: Applications in the Rapid and Facile Synthesis of Oligonucleotides, Analogs, and Conjugates." Tetrahedron 53(8): 2731–50 (1997).

Kern, D.L., et al. "9–$\beta$–D–Ribopyranosylhypoxanthine, A Minor Component Produced by *Streptomyces Antibioticus*." J. Heterocyclic Chem. 17: 461–63 (1980).

Lewis, A., et al. "Derivatives of the Nucleoside Antibiotics, Toyocamycin and Sangivamycin, Analogs of N6–($\Delta^2$–Isopentenyl)adenosine." J. Heterocyclic Chem. 11: 71–72 (1974).

Nagatsugi, F., et al. "2–Aminopurine Derivatives with C6–Substituted Olefin as Novel Cross–linking Agents and the Synthesis of the Corresponding $\beta$–Phosphoramidite Precursors." Tetrahedron 53(9): 3035–44 (1997).

Pitsch, Stefan, et al. "Pyranosyl–RNA ('p–RNA'): Base Pairing Selectivity and Potential to Replicate." Helvetica Chemica Acta 78: 1621–35 (1995).

Taylor, M., et al. "Ribose–Modified Adenosine Analogues as Adenosine Receptor Agonists." J. Med. Chem. 29: 346–53 (1986).

Torrence, Pail F., et al. "5–O–Alkylated Derivatives of 5–Hydroxy–2'–deoxyuridine as Potential Antiviral Agents: Anti–Herpes Activity of 5–Propynyloxy–2'–deoxyuridine." J. Med. Chem. 21(2): 228–31 (1978).

Watanabe, K.A., et al. "Nucleosides. LXXXVII. Total Synthesis of Pentopyranine A, an $\alpha$–L Cytosine Nucleoside Elaborated by *Streptomyces griseochromogenes*." J. Org. Chem. 39(17): 2482–86 (1974).

Xia, Xiaoyang, et al. "Stereo–controlled Synthesis of $\beta$–2'–deoxypyrimidine Nucleosides via Intrammolecular Glycosolations." Tetrahedron Letter 38(7): 1111–14 (1997).

* cited by examiner

LINKER NUCLEOSIDE, AND PRODUCTION AND USE OF THE SAME

The present invention relates to a linker nucleoside, its preparation and use for the covalent bonding of biomolecules to oligonucleotides, in particular p-RNA oligonucleotides.

Pyranosylnucleic acids (p-NAs) are in general structures isomeric to the natural RNA, in which the pentose units are present in the pyranose form and are repetitively linked between the positions C-2' and C-4' by phosphodiester groups (FIG. 1). "Nucleobase" is understood here as meaning the canonical nucleobases A, T, U, C, G, but also the pairs isoguanine/isocytosine and 2,6-diaminopurine/xanthine and, within the meaning of the present invention, also other purines and pyrimidines. p-NAs, namely the p-RNAs derived from ribose, were described for the first time by Eschenmoser et al. (Pitsch, S. et al. Helv. Chim. Acta 1993, 76, 2161; Pitsch, S. et al. Helv. Chim Acta 1995, 78, 1621; Angew. Chem. 1996, 108, 1619–1623). They exclusively form so-called Watson-Crick-paired, i.e. purine-pyrimidine- and purine-purine-paired, antiparallel, reversibly "melting", quasi-linear and stable duplexes. Homochiral p-RNA strands of the opposite sense of chirality likewise pair controllably and are strictly non-helical in the duplex formed. This specificity, which is valuable for the synthesis of supramolecular units, is connected with the relatively low flexibility of the ribopyranose phosphate backbone and also with the strong inclination of the base plane to the strand axis and the tendency resulting from this for intercatenary base stacking in the resulting duplex and can finally be attributed to the participation of a 2',4'-cis-disubstituted ribopyranose ring in the synthesis of the backbone. These significantly better pairing properties make p-NAs preferred pairing systems, compared with DNA and RNA, for use in the synthesis of supramolecular units. They form a pairing system which is orthogonal to natural nucleic acids, i.e. they do not pair with DNAs and RNAs occurring in the natural form, which is particularly of importance in the diagnostic field.

Eschenmoser et al. (1993, supra) has for the first time prepared a p-RNA, as shown in FIG. 2 and explained below.

In this connection, a suitable protected nucleobase was reacted with the anomer mixture of the tetrabenzoylribopyranose by action of bis(trimethylsilyl)acetamide and a Lewis acid such as, for example, trimethylsilyl trifluormethanesulphonate (analogously to H. Vorbrüggen, K. Krolikiewicz, B. Bennua, Chem. Ber. 1981, 114, 1234.). Under the action of base (NaOH in THF/methanol/water in the case of the purines; saturated ammonia in MeOH in the case of the pyrimidines), the acyl protective groups were removed from the sugar, and the product was protected in the 3',4'-position under acidic catalysis with p-anisaldehyde dimethyl acetal. The diastereomer mixture was isolated in the 2'-position, the 3', 4'-methoxybenzylidene-protected 2'-benzoate was deacetalized by acidic treatment, e.g. with trifluoroacetic acid in methanol, and reacted with dimethoxytrityl chloride. The 2'→3' migration of the benzoate was initiated by treatment with p-nitrophenol/4-(dimethylamino)pyridine/triethylamine/pyridine/n-propanol. Almost all reactions were worked up by column chromatography. The key structural unit synthesized in this way, the 4'-DMT-3'-benzoyl-1'-nucleobase derivative of the ribopyranose, was then partly phosphitylated or bonded to a solid phase via a linker.

In the subsequent automated oligonucleotide synthesis, the carrier-bonded component in the 4'-position was repeatedly acidically deprotected, a phosphoramidite was coupled on under the action of a coupling reagent, e.g. a tetrazole derivative, still-free 4'-oxygen atoms were acetylated and the phosphorus atom was oxidized in order thus to obtain the oligomeric product. The remaining protective groups were then removed, and the product was purified and desalted by means of HPLC.

The disadvantage of the already known p-RNA oligonucleotides is that no methods are known to covalently bond other biomolecules to these oligonucleotides.

It was therefore the object of the present invention to make available suitable constructs which make possible covalent bonding of other biomolecules to oligonucleotides, in particular to p-RNA oligonucleotides.

A subject of the present invention is therefore a linker nucleoside of the formula (I) or (II),

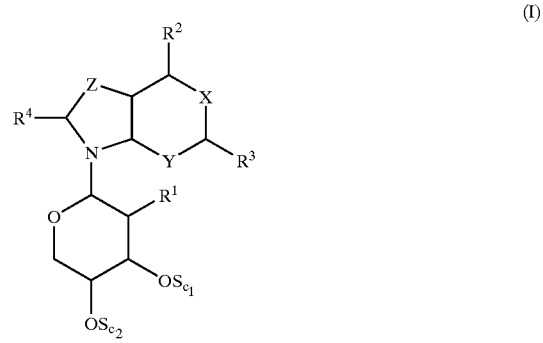

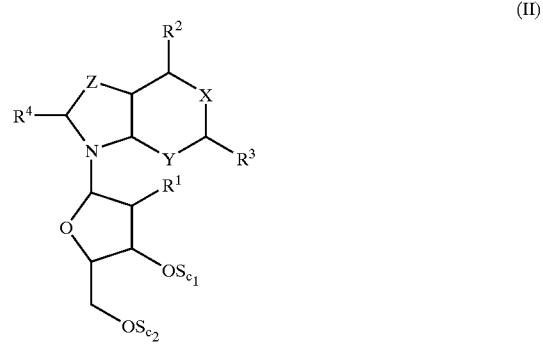

in which $R^1$ is equal to H, OH, phosphoramidite, Hal where Hal is preferably equal to Br or Cl,
$R^2$, $R^3$ and $R^4$ independently of one another, identically or differently, in each case are $OC_nH_{2n-1}$ for formula (I) or $(C_nH_{2n})NR^{10}R^{11}$ for formula (I) and (II) where $R^{10}R^{11}$ is linked via a radical of the formula

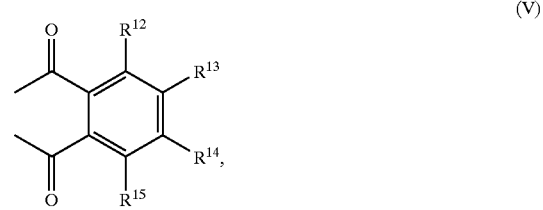

in which $R^{12}$, $R^{13}$, $R^{14}$ and $R^{15}$ independently of one another, identically or differently, in each case are H, $C_nH_{2n+1}$ or $C_nH_{2n-1}$ or $OR^7$, where $R^7$ is equal to H, $C_nH_{2n-1}$ or $C_nH_{2n-1}$, —C(O)R where $R^8$ is equal to a linear or branched, optionally substituted alkyl or aryl radical, preferably a phenyl radical, where n is equal to an integer from 1–12, preferably 1–8, in particular 1–4, X, Y and Z independently of one another, identically or differently, in each case are =N—, =C(R$^9$)— or —N(R$^9$)— where R$^9$ and R$^{9'}$ independently of one another, identically or differently, in each case are H or $C_nH_{2n+1}$ or $(C_nH_{2n})$NR$^{10}$R$^{11}$ having the abovementioned meanings, in a particular embodiment the radicals R$^2$, R$^3$ and R$^4$ and the atoms X, Y and Z taken together have the meaning assigned to them by the structure of the linker nucleoside of the formula (I) or (II) as a pentopyranosyl- or pentofuranosylpurine, -2,6-diaminopurine, -6-purinthiol, -adenosine, -guanosine, -isoguanosine, -6-thioguanosine, -xanthine, -hypoxanthine, -indole, -tryptamine, -N-phtaloyl-tryptamine, -caffeine, -theobromine, -theophylline or benzotriazole, and $S_{c1}$ and $S_{c2}$ independently of one another, identically or differently, in each case are H or a protective group selected from an acyl, trityl or allyloxycarbonyl group, preferably a benzoyl or 4, 4'-dimethoxytrityl (DMT) group, or a phosphoester (III), phosphoester(V), thiophosphate(V), phosphonate or phosphoramidite,
or of the formula (III) or (IV)

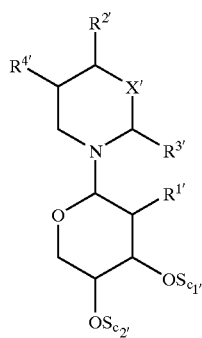

(III)

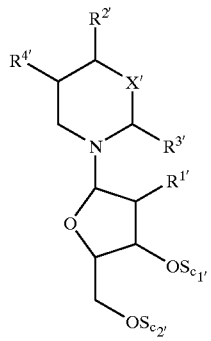

(IV)

in which R$^{1'}$ is equal to H, OH, phosphoramidite or Hal where Hal is preferably equal to Br or Cl, R$^{2'}$,R$^{3'}$ and R$^{4'}$ independently of one another, identically or differently, in each case for formula (III) $OC_nH_{2n-1}$ where n is equal to an integer from 1–12, preferably 1–8, in particular 1–4, or for formula (III) and (IV) $(C_nH_{2n})$NR$^{10'}$R$^{11'}$, where R$^{11'}$, independently of one another has the abovementioned meaning of R$^{10}$ or R$^{11}$, and X' in each case is =N—, =C(R$^{9'}$)— or —N(R$^{9''}$)—, where R$^{9'}$ and R$^{9''}$ independently of one another have the above-mentioned meaning of R$^9$ and R$^{9'}$, in a particular embodiment the radicals R$^{2'}$, R$^{3'}$ and R$^{4'}$ and the atom X taken together have the meaning assigned to it by the structure of the linker nucleoside of the formula (III) or (IV) as a pentopyranosyl- or pentofuranosylpyridine, -pyrimidine, -thymidine, -cytosine, -isocytosine, -uracil, and $S_{c1'}$ and $S_{c2'}$ have the abovementioned meaning of $S_{c1}$ and $S_{c2}$.

The pentose according to the invention is in general a ribose, arabinose, lyxose and/or xylose, preferably a ribopyranose, where the pentopyranosyl moiety can have the D configuration, but also the L configuration.

Customarily, the linker nucleoside according to the invention is a pentopyranosyl- or pentofuranosylpurine, -2,6-diaminopurine, -6-purinthiol, -pyridine, -pyrimidine, -adenosine, -guanosine, -isoguanosine, -6-thioguanosine, -xanthine, -hypoxanthine, -thymidine, -cytosine, -isocytosine, -indole, -tryptamine, -N-phthaloyltryptamine, -uracil, -caffeine, -theobromine, -theophylline, -benzotriazol or -acridine, in particular a pentopyranosylpurine, -pyrimidine, -adenosine, -guanosine, -thymidine, -cytosine, -tryptamine, -N-phthalotryptamine or -uracil.

The linker nucleosides according to the invention are consequently compounds having functional groups which can covalently bond biomolecules, to, for example, nucleic acids occurring in their natural form or modified nucleic acids, such as DNA, RNA but also p-NAs, preferably pRNAs. For p-NAs, this is particularly advantageous, as in this case no linkers are yet known.

For example, among these are pentopyranosylnucleosides in which R2, R3, R4, R2', R3' and/or R4' for formula (I), (II), (III) and (IV) is a 2-phthalimidoethyl or, for formula (I) and (Im), an allyloxy radical. Preferred uracil-based linkers according to the present invention are, for example, those in which the 5-position of the uracil has preferably been modified, e.g. N-phthaloylaminoethyluracil, but also indole-based linkers, preferably tryptamine derivatives, such as, for example, N-phthaloyltryptamine.

In a particular embodiment, for example, a linker according to formula (III) or (IV), in which R4' is (CnH2n)NR10'R11' and R10'R11' is linked to the meaning already designated via a radical of the formula (V), is advantageously prepared by the following process:

(a) a compound of the formula (III) or (IV) where R$^{4'}$ is equal to $(C_nH_{2n})OS_{c3}$ or $(_nH_{2n})$Hal, in which n has the abovementioned meaning, $S_{c3}$ is a protective group, preferably a mesylate group, and Hal is chlorine or bromine, is reacted with an azide, preferably in DMF, then (b) the reaction product from (a) is reduced, preferably using triphenylphosphine e.g. in pyridine, then (c) the reaction product from (b) is reacted with an appropriate phthalimide, e. g. N-ethoxycarbonylphthalimide, and (d) the reaction product from (c) is reacted with an appropriate protected pentose, e.g. ribose tetrabenzoate, and finally (e) the protective groups are optionally removed, e.g. using methylate, and the product is then optionally converted into a phosphorylated unit which is suitable for oligonucleotide synthesis.

In addition, indole derivatives as linkers have the advantage of the ability to fluoresce and are therefore particularly preferred for nanotechnology applications which may concern the detection of very small amounts of substance. Thus indole-1-ribosides have already been described in N. N. Suvorov et al., Biol. Aktivn. Soedin., Akad. Nauk SSSR 1965, 60 and Tetrahedron 1967, 23, 4653. However, there is no analogous process for preparing 3-substituted derivates. In general, they are prepared via the formation of an aminal of the unprotected sugar component and an indoline, which is then converted into the indole-1-riboside by oxidation. The indole-1-glucoside and -1-arabinoside, for example, whose 3-substituted derivates were usually prepared by means of Vielsmeier reaction, have been described (Y. V. Dobriynin et al, Khim.-Farm. Zh. 1978, 12, 33). This way of introducing aminoethyl units into the 3-position of the indole is too complicated, however, for industrial application.

In a further particular embodiment, a linker according to formula (I) or (II), in which X and Y independently of one another, identically or differently, in each case are =C(R16) where R16 is equal to H or CnH2n and Z is =C(R16)— where R16 is equal to (CnH2n)NR10R11 is therefore advantageously prepared, for example, by the following process:

(a) the corresponding indoline, e.g. N-phthaloyltryptamine, is reacted with a pentose, e.g. D-ribopyranose, to give the nucleoside triol, then (b) the hydroxyl groups of the pentose moiety of the product from (a) are preferably protected with acyl groups, e.g. by means of acetic anhydride, then (c) the product from (b) is oxidized, e.g. by means of 2,3-dichloro-5,6-dicyanoparaquinone, and (d) if appropriate, the hydroxyl protective groups of the pentose moiety of the product from (c) are removed, for example by means of methylate, and then optionally converted into a phosphorylated unit which is suitable for oligonucleotide synthesis.

The processes described, however, cannot only be used in the case of ribopyranose, but also in the case of ribofuranose and 2'-deoxyribofuranoses or 2'-deoxyribopyranoses, which is particularly advantageous. As a nucleosidation partner of the sugars, tryptamine, in particular N-acyl derivates of tryptamine, especially N-phthaloyltryptamine, is preferably used. The remaining linker nucleosides can be prepared in an analogous manner or a manner known to the person skilled in the art.

In a further embodiment, the 4'-protected, preferably the 3', 4'-protected linker nucleosides are phosphitylated in a further step or bonded to a solid phase.

The phosphitylation is effected, for example, by means of monoallyl N-diisopropylchlorophosphoramidite in the presence of a base, e.g. N-ethyldiisopropylamine. The bonding of a protected pentopyranosylnucleoside according to the invention to a solid phase, e.g. "long-chain-alkylamino-controlled pore glass" (CPG, Sigma Chemie, Munich) can be carried out, for example, as described in Eschenmoser et al. (1993).

The compounds obtained serve, for example, for the preparation of pentopyranosylnucleic acids, which contain one of the linkers according to the invention.

A further subject of the present invention is therefore a process for the preparation of a nucleic acid, having the following steps:

(a) in a first step a protected nucleoside or a protected linker nucleoside is bonded to a solid phase and (b) in a second step the 3'-, 4'-protected nucleoside bonded to a solid phase according to step (a) is lengthened by a phosphitylated 3'-, 4'-protected nucleoside or linker nucleoside, then oxidized, for example, by an aqueous iodine solution, and (c) step (b) is repeated using identical or different nucleosides or linker nucleosides until the desired nucleic acid is present, the nucleic acid containing at least one inventive linker nucleoside.

A suitable coupling reagent is particularly benzimidazolium triflate, preferably after recrystallizing in acetonitrile and after dissolving in acetonitrile, as in contrast to 5-(4-nitrophenyl)-1H-tetrazole as a coupling reagent no blockage of the coupling reagent lines and contamination of the product takes place.

Furthermore, it is advantageous by means of addition of a salt, such as sodium chloride, to the protective-group-removing hydrazinolysis of oligonucleotides, in particular of p-NAs, preferably of p-RNAs, to protect pyrimidine bases, especially uracil and thymine, from a ring-opening which would destroy the oligonucleotide. Allyoxy groups can preferably be removed by palladium [Pd(O)] complexes e.g. before hydrazinolysis.

In a further particular embodiment, pentofuranosyl nucleosides, e.g. adenosine, guanosine, cytidine, thymidine and/or uracil occurring in their natural form, in addition to pentopyranosylnucleosides, can also be incorporated in step (a) and/or step (b), which leads, for example, to a mixed p-NA-DNA or p-NA-RNA.

In another particular embodiment, in a further step an allyloxy linker of the formula

$$S_{c4}NH(C_nH_{2n})CH(OPS_{c5}S_{c6})C_nH_{2n} \, OS_{c7} \qquad (VI),$$

in which $S_{c4}$ and $S_{c7}$ independently of one another, identically or differently, are in each case a protective group in particular selected from Fmoc and/or DMT, $S_{c5}$ and $S_{c6}$ independently of one another, identically or differently, are in each case an allyloxy and/or diisopropylamino group, can be incorporated. n has the meaning already mentioned above.

The present invention therefore also extends to an allyloxy linker of the formula

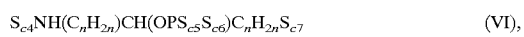

$$S_{c4}NH(C_nH_{2n})CH(OPS_{c5}S_{c6})C_nH_{2n}S_{c7} \qquad (VI),$$

in which $S_{c4}$ and $S_{c7}$ independently of one another, identically of differently, are in each case a protective group in particular selected from Fmoc and/or DMT, $S_{c5}$ and $S_{c6}$ independently of one another, identically or differently, are in each case an allyloxy and/or diisopropylamino group and n is as designated above.

A particularly preferred allyloxy linker is (2-(S)-N-Fmoc-O1-DMT-O2-allyloxydiisopropylaminophosphinyl-6-amino-1,2-hexanediol).

Starting from, for example, lysine, it is thus possible in a few reaction steps to synthesize amino-terminal linkers which carry both an activatable phosphorus compound and an acid-labile protective group, such as DMT, and can therefore be easily used in automatable oligonucleotide synthesis (see, for example, P. S. Nelson et al., Nucleic Acid Res. 1989, 17, 7179; L. J. Arnold et al., WO 8902439). The repertoire was extended in the present invention by means of a lysine-based linker in which, instead of the otherwise customary cyanoethyl group on the phosphorus atom, an allyloxy group has been incorporated, and which can therefore be employed advantageously in the Noyori oligonucleotide method (R. Noyori, J. Am. Chem. Soc. 1990, 112, 1691–6).

In another particular embodiment, in a further step a lysine linker of the formula

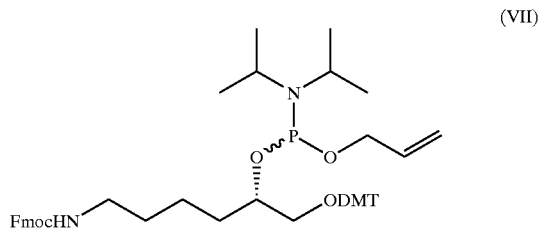

(VII)

can be incorporated.

The present invention therefore also extends to a lysine linker of the formula

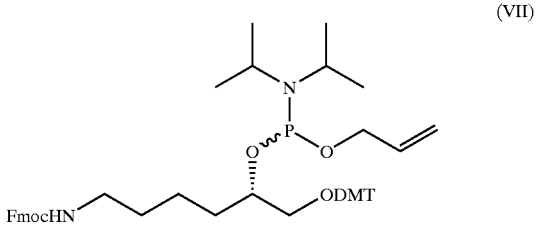

(VII)

A further subject of the present invention is therefore also a nucleic acid which contains at least one linker nucleoside according to the invention and optionally at least one allyloxy linker according to the invention. A pentopyranosylnucleic acid is particularly preferred, as p-NAs and in particular the p-RNAs form stable duplexes with one another and in general do not pair with DNAs and RNAs occurring in their natural form. This property makes p-NAs preferred pairing systems.

Such pairing systems are supramolecular systems of non-covalent interaction, which are distinguished by selectivity, stability and reversibility, and whose properties are preferably influenced thermodynamically, i.e. by temperature, pH and concentration. Such pairing systems can also be used, for example, on account of their selective properties as a "molecular adhesive" for the bringing together of different metal clusters to give cluster associates having potentially novel properties [see, for example, R. L. Letsinger, et al., Nature 1996, 382, 607–9; P. G. Schultz et al., Nature 1996, 382, 609–11]. Consequently, the p-NAs are also suitable for use in the field of nanotechnology, for example for the production of novel materials, diagnostics and therapeutics and also microelectronic, photonic and optoelectronic components and for the controlled bringing together of molecular species to give supramolecular units, such as, for example, for the (combinatorial) synthesis of protein assemblies [see, for example, A. Lombardi, J. W. Bryson, W. F. DeGrado, Biopolymers (Pept. Sci.) 1997, 40, 495–504], as p-NAs form pairing systems which are strongly and thermodynamically controllable. A further application therefore especially arises in the diagnostic and drug discovery field due to the possibility of providing functional, preferably biological, units such as proteins or DNA/RNA sections, with a p-NA code which does not interfere with the natural nucleic acids (see, for example, WO93120242).

A further subject of the present invention is a conjugate comprising a linker nucleoside according to the invention or an inventive nucleic acid and a biomolecule.

Biomolecule is understood according to the present invention as antibody or functional moieties thereof or an enzyme, and also a nucleic acid such as DNA or RNA, or cell constituents such as lipids, glycoproteins, filaments constituents, or viruses, virus constituents such as capsids, viroids, and their derivatives such as, for example, acetates. Functional moieties of antibodies are, for example, Fv fragments (Skerra & Plückthun (1988) Science 240, 1038), single-chain Fv fragments (scFv; Bird et al (1988) Science 242, 423; Huston et al. (1988) Proc. Natl. Acad. Sci. U.S.A., 85, 5879) or Fab fragments (Better et al. (1988) Science 240, 1041).

The conjugates according to the invention of effector molecules and preferably peptide, but in contrast to PNA, selective and controllable pairing systems are advantageous if reversibly supramolecular assemblies are to be synthesized, whose action, such as, for example, binding, inhibition, induction of a physiological effect, differs from the action of the individual effector molecules.

An attempt to use peptide "adhesive" units for the formation of homo- or heterodimeric assemblies is described, for example, in WO 94/28173:

Association peptides (hexa- or heptapeptides) of a fixed sequence bring together effector units, such as, for example, proteins, to give supramolecular units. Such a method can maintain higher flexibility by means of controllability of this association process, which in general cannot be realized with the association peptides, but advantageously with the pairing systems of the present invention.

Thus, for example, WO 96/13613 describes a method for finding a substance which induces a biological action due to the multimerization of proteins by first determining a substance I by means of a test, which substance binds to a protein, then determining a second substance II which binds to a second protein and then linking the two substances I and II covalently via a linker such that dimerization of the two proteins is induced. This dimerization then brings about the desired biological effect. Such a method can maintain greater flexibility if the linking of the two substances I and II does not take place covalently, but by means of a pairing system such as the oligomer or conjugate according to the invention. As a result of the controllability of this pairing, for example by means of temperature or pH, the dimerization process of the proteins can be observed or its extent can be controlled. The pairing systems according to the invention have the advantage, for example, compared with the systems from WO 96/13522, that they are nuclease-stable.

A biomolecule, e.g. DNA or RNA, can be used for non-covalent linking to another biomolecule, e.g. DNA or RNA if both biomolecules contain sections which can bind to one another by formation of hydrogen bridges as a result of complementary sequences of nucleobases. Biomolecules of this type are found, for example, in analytical systems for signal amplification units, where a DNA molecule whose sequence is to be analyzed is immobilized on a solid carrier by means of such a non-covalent DNA linker on the one hand, and on the other hand is to be bonded (see, for example, S. Urdea, Bio/Technol. 1994, 12, 926 or U.S. Pat. No. 5,624,802) to a signal-amplifying branched DNA molecule (bDNA). A significant disadvantage of the last-described systems is that they are subject to date to the process for nucleic acid diagnosis by means of polymerase chain reaction (PCR) (K. Mullis, Methods Enzymol. 1987, 155, 335) with respect to sensitivity. This is to be attributed, inter alia, to the fact that the non-covalent bonding of the solid carrier to the DNA molecule to be analyzed does not always take place specifically, just like the non-covalent bonding of the DNA molecule to be analyzed, as a result of which a mixing of the functions "sequence recognition" and "non-covalent bonding" occurs. The use of p-NAs as an orthogonal pairing system which does not intervene in the DNA or RNA pairing processes solves this problem advantageously, as a result of which the sensitivity of the analytical processes described can be markedly increased.

In a preferred embodiment, what is concerned here are p-RNA/DNA or p-RNA/RNA conjugates.

Conjugates are preferably used if the functions "sequence recognition" and "non-covalent bonding" have to be realized in one molecule, as the conjugates according to the invention contain two pairing systems which are orthogonal to one another.

Both sequential and convergent processes are suitable for the preparation of conjugates.

In a sequential process, for example, after automated synthesis of a p-RNA oligomer has taken place directly on the same synthesizer—after readjustment of the reagents and of the coupling protocol—e.g. a DNA oligonucleotide is further synthesized. This process can also be carried out in the reverse sequence.

In a convergent process, for example, p-RNA oligomers having amino-terminal linkers and, for example, DNA oligomers are synthesized in separate processes using, for example, thiol linkers. An iodoacetylation of the p-RNA oligomer and the coupling of the two units according to protocols known from the literature is preferably then carried out (T. Zhu et al., Bioconjug. Chem. 1994, 5, 312).

Convergent processes have proved to be particularly preferred on account of their flexibility.

The term conjugate within the meaning of the present invention is also understood as meaning so-called arrays. Arrays are arrangements of immobilized recognition species which, especially in analysis and diagnosis, play an important role in the simultaneous determination of analytes. Examples are peptide arrays (Fodor et al., Nature 1993, 364, 555) and nucleic acid arrays (Southern et al. Genomics 1992, 13, 1008; Heller, U.S. Pat. No. 5,632,957). A higher flexibility of these arrays can be achieved by bonding the recognition species to coding oligonucleotides and the associated, complementary strands to certain positions on a solid carrier. By applying the coded recognition species to the "anti-coded" solid carrier and adjustment of hybridizaton conditions, the recognition species are non-covalently bonded to the desired positions. As a result, various types of recognition species, such as, for example, DNA sections, antibodies, can be arranged simultaneously on a solid carrier only by use of hybridization conditions (see FIG. 4.). As a prerequisite for this, however, codons and anticodons are necessary which are extremely strong, selective—in order to keep the coding sections as short as possible—and do not interfere with natural nucleic acid. p-NAs, preferably p-RNAs, are particularly advantageously suitable for this.

Another subject of the present invention is therefore a carrier on which is immobilized at least one linker nucleoside according to the invention, at least one nucleic acid according to the invention and/or at least one conjugate according to the invention.

The term "immobilized" is understood within the meaning of the present invention as meaning the formation of a covalent bond, quasi-covalent bond or supramolecular bond by association of two or more molecular species such as molecules of linear constitution, in particular peptides, peptoids, proteins, linear oligo- or polysaccharides, nucleic acids and their analogues, or monomers such as heterocycles, in particular nitrogen heterocycles, or molecules of non-linear constitution such as branched oligo- or polysaccharides or antibodies and their functional moieties such as Fv fragments, single chain Fv fragments (scFv) or Fab fragments.

Suitable carrier materials are, for example, ceramic, metal, in particular noble metal, glasses, plastics, crystalline materials or thin layers of the carrier, in particular of the materials mentioned, or (bio)molecular filaments such as cellulose, structural proteins.

A further subject of the present invention also relates to a diagnostic comprising a linker nucleoside according to the invention, a nucleic acid according to the invention or a conjugate according to the invention, as already described in greater detail above.

Another subject of the invention is therefore the use of a linker nucleoside according to the invention, of a nucleic acid according to the invention, of a conjugate according to the invention and/or of a carrier according to the invention for the production of a pharmaceutical, such as, for example, of a therapeutic, of a diagnostic and/or of an electronic component.

The invention also relates to the use of the linker nucleosides according to the invention, of the nucleic acid according to the invention or of the conjugate according to the invention and/or of the carrier according to the invention in a pairing and/or test system, such as described in greater detail, for example, in WO94/28173, WO96/13522, WO96/13613, R. L. Letsinger, et al., Nature, 1996, 382, 607-9; P. G. Schultz et al., Nature, 1996, 382, 609–11 or A. Lombardi, J. W. Bryson, W. F. DeGrado, Biopolymers (Pept. Sci.) 1997, 40, 495–504 and generally explained above.

The following figures and examples are intended to describe the invention in greater detail, without restricting it.

EXAMPLES

Synthesis of p-RNA Linker Systems

Figure 1:
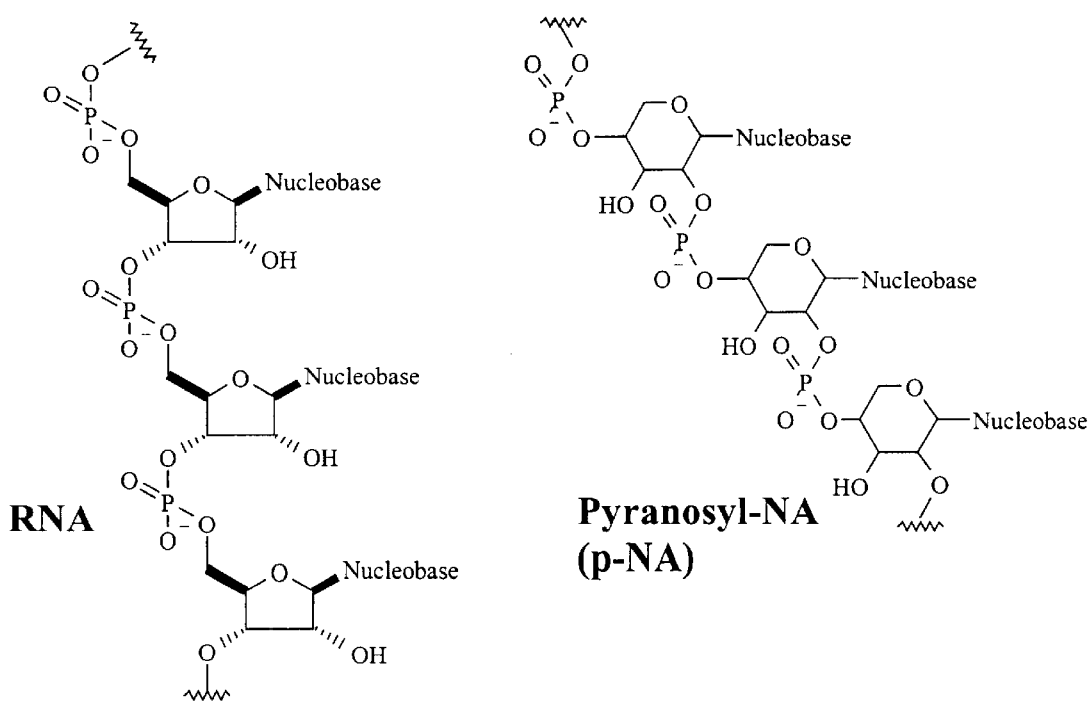
FIG. 1 shows a section of the structure of RNA in its naturally occurring form (left) and in the form of a p-NA (right).
Figure 2A:
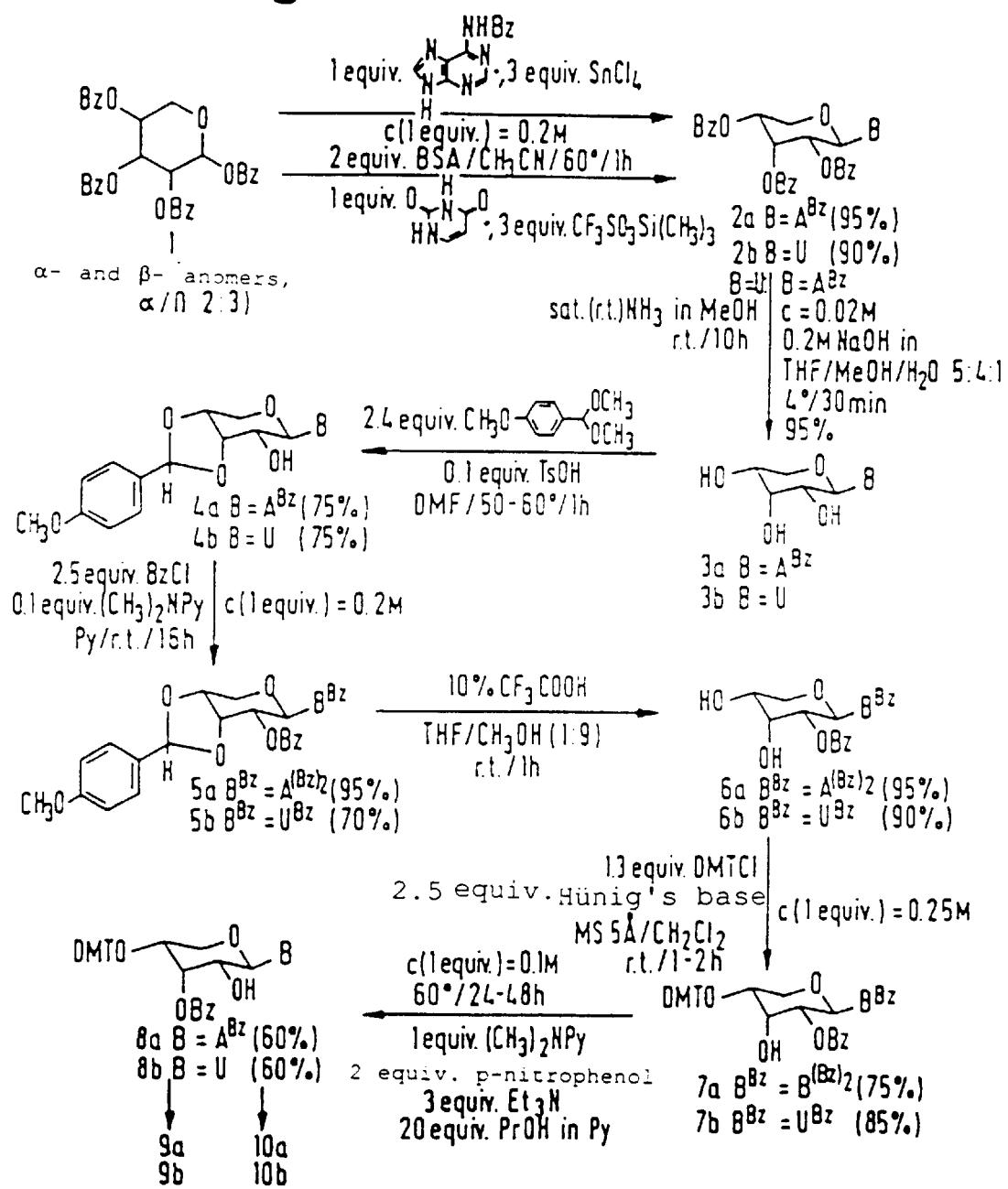
FIG. 2A schematically shows the synthesis of a p-Ribo (A,U)-oligonucleotide according to Eschenmoser et al. (1993).
Figure 2B:
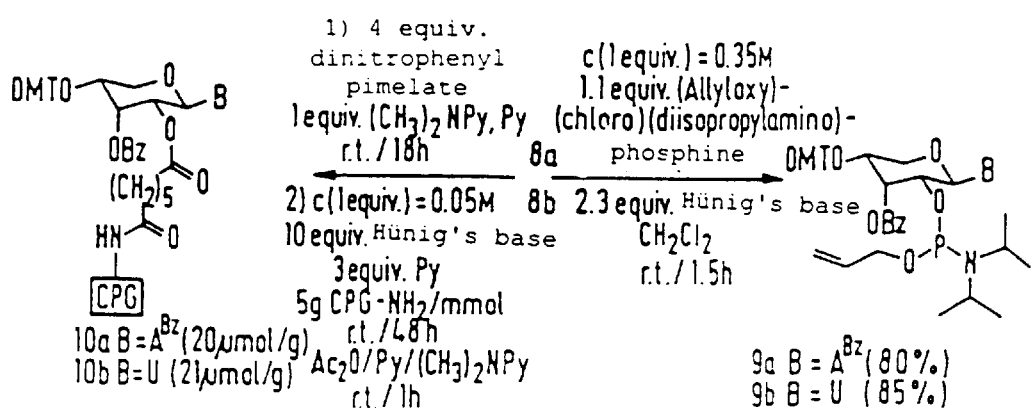
FIG. 2B schematically shows the synthesis of a p-Ribo (A,U)-oligonucleotide according to Eschenmoser et al. (1993).
Figure 2B:
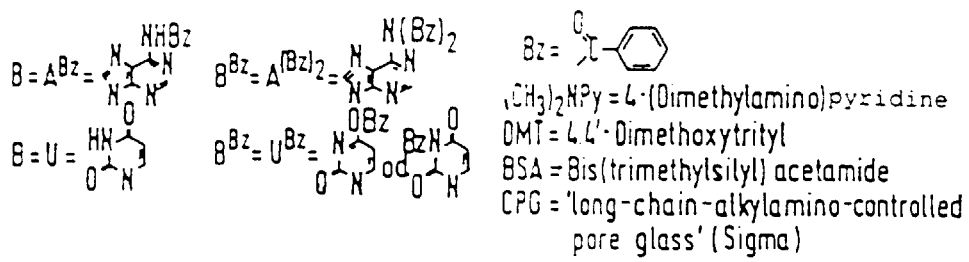
Figure 3:
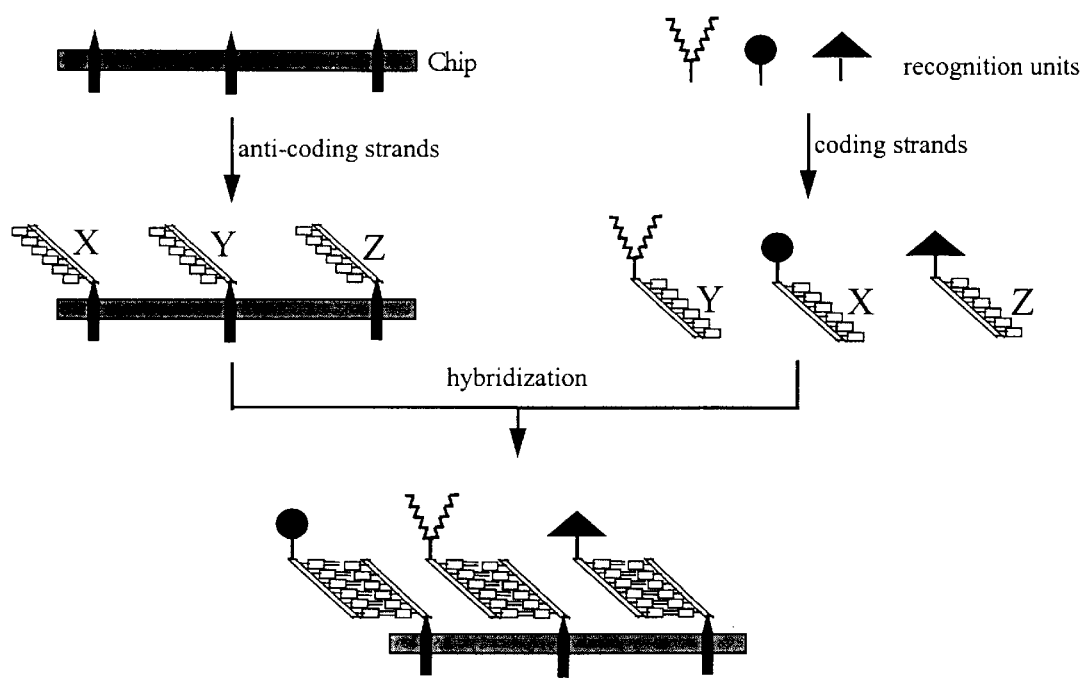
FIG. 3 schematically shows an arrangement of immobilized recognition structures (arrays) on a solid carrier.

Below, three ways are described which make possible the provision of linkers which have an amino terminus, which can then be used for the linking of functional units:

Example 1

Uracil-based Linker

On the basis of the modification of the 5-position of the uracil. The preparation of hydroxyethyluracil 28 is possible on a large scale according to a known method (J. D. Fissekis, A. Myles, G. B. Brown, J. Org. Chem. 1964, 29, 2670. g-Butyrolactone 25 was formylated with methyl formate, the sodium salt 26 was reacted to give the urea derivative 27 and this was cyclized to the hydroxyethyluracil 28 (Scheme 1).

Scheme 1: Synthesis of hydroxyethyluracil 28

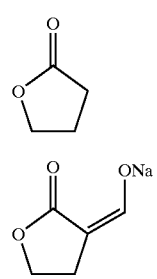

-continued

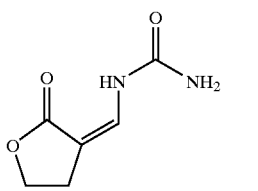

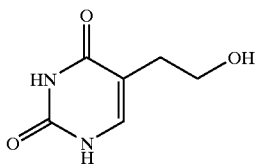

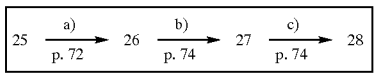

a) NaOMe, HCOOMe, Et₂O, 72%; b) urea, H⁺, H₂O, 49%; c) NaOEt, EtOH, Δ, 36%.

Scheme 2: Synthesis of N-phtaloylaminoethyluracil 32

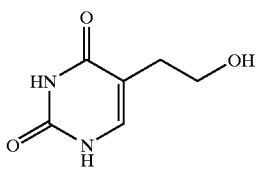

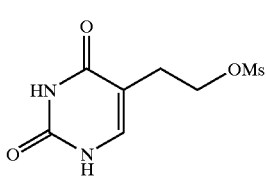

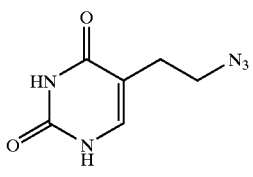

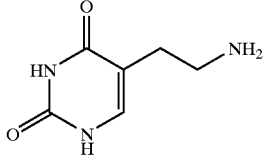

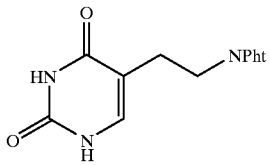

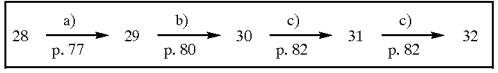

a) MsCl, py, 0°, 50%; b) NaN₃, DMF, 60°, 71%; c) 1. PPh₃, py; 2. NH₃/H₂O, 85%; d) PhtNCO₂Et, Na₂CO₃, H₂O, 91%.

Hydroxyethyluracil 28 was methylated with methanesulphonyl chloride in pyridine to give 29 (J. D. Fissekis, F. Sweet, J. Org. Chem. 1973, 38, 264).

The following stages have been newly invented: using sodium azide in DMF, 29 was reacted to give the azide 30 and this was reduced with triphenylphosphine in pyridine to give the aminoethyluracil 31. The amino function in 31 was finally protected with N-ethoxycarbonylphtalimide (Scheme 2). Nucleosidation of ribose tetrabenzoate 33 with N-phtaloylaminoethyluracil 32 produced the ribose tribenzoate 34 in good yields. The anomeric centre of the pyranose ring is in the β configuration, as can be clearly seen from the coupling constants between H—C(1') and H—C(2') of J=9.5 Hz. Subsequent removal of the benzoate protective groups using NaOMe in MeOH yielded the linker triol 35. 35 was reacted with benzoyl chloride at −78° C. in pyridine/dichlormethane 1:10 in the presence of DMAP. In this process, in addition to the desired 2'-benzoate 36 (64%), 2',4'-dibenzoylated product (22%) was also obtained, which was collected and converted into the triol 35 analogously to the methanolysis of 34 to 35. The 2'-benzoate 36 was tritylated with dimethoxytrityl chloride in the 4'-position in yields of greater than 90% in the presence of Hünig's base in dichloromethane. The rearrangement of 4'-DMT-2'-benzoate 37 to the 4'-DMT-3'-benzoate 38 was carried out in the presence of DMAP, p-nitrophenol and Hünig's base in n-propanol/pyridine 5:2. After chromatography, 38 is obtained. 4'-DMT-3'-benzoate 38 was finally reacted with ClP (OAll)N(iPr)₂ to give the phosphoramidite 39 in the presence of Hünig's base (Scheme 3). This can be employed for the automated oligonucleotide synthesis without alteration of the synthesis protocols.

Scheme 3: Synthesis of the linker phosphoramidite 39

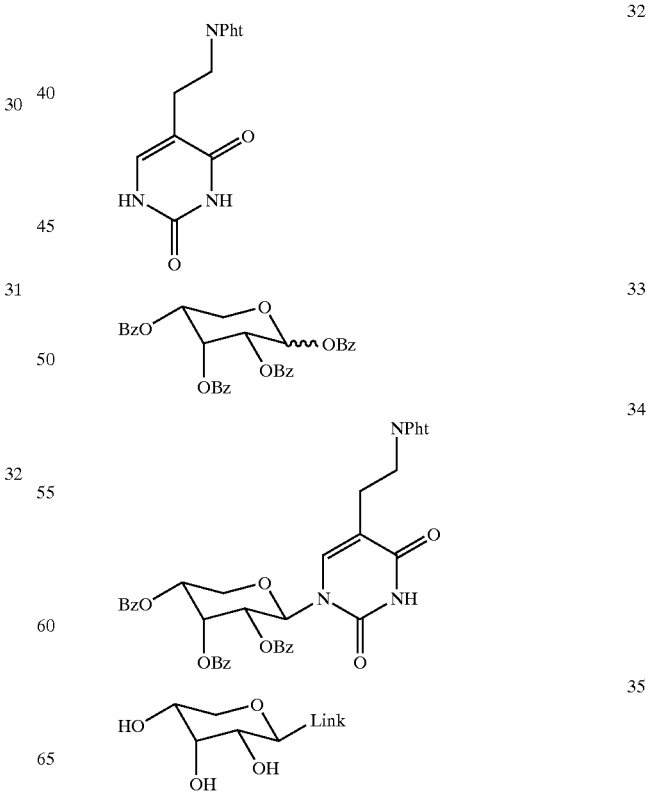

-continued

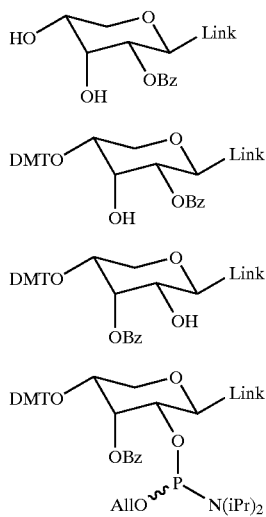

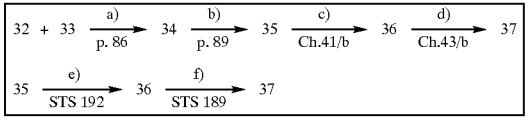

a) BSA, TMSOTf, CH₃CN, 50°, 86%; b) NaOMe, MeOH, 93%; c) BzCl, py/CH₂Cl₂, -78°; d) DMTCl, EtNiPr₂, CH₂Cl₂; e) DMAP, pNO₂phenol, EtNiPr₂, py, nPrOH, 70°; f) ClP(OAll)NiPr₂, EtNiPr₂, CH₂Cl₂.

Implementation

Synthesis of a Uracil Linker Unit 5-(2-Azidoethyl)uracil (30)

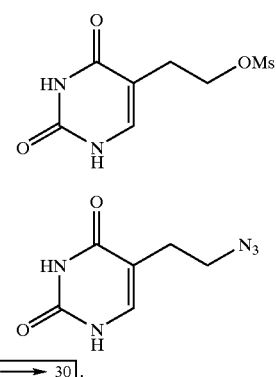

1. Procedure 26.0 g (0.11 mol) of 29 were dissolved in 250 ml of DMF in a 500 ml three-necked flask equipped with an internal thermometer and reflux condenser and treated with 10.8 g (0.166 mol) of sodium azide. The suspension was subsequently stirred at 60° C. for four hours ((TLC checking, CHCl₃/MeOH 9:1). The DMF was distilled off and the residue was stirred with 150 ml of water. The solid was filtered off, washed with about 50 ml of water and dried over phosphorus pentoxide overnight in vacuo in a desiccator. 14.2 g (71%) of 30 were obtained in the form of a colourless solid of m.p. 230–235° C. (with dec.).

2. Analytical Data 5-(2-Azidoethyl)uracil (30)

M.p.: 230–235° C. with decomp. TLC: CHCl₃/MeOH 9:1, $R_f$ 0.48. UV (MeOH): $\lambda_{max}$ 263.0 (7910). IR (KBr): 3209s, 3038s, 2139s, 1741s, 1671s, 1452m, 1245m, 1210m. ¹H-NMR (300 MHz, d₆-DMSO): 2.46 (t, 2H, J(CH₂CH₂N, CH₂CH₂N)=7.0, CH₂CH₂N); 3.40 (t, 2H, J(CH₂CH₂N, CH₂CH₂N)=7.0, CH₂CH₂N); 7.36 (s, H—C(6)); 11.00 (br. s, 2H, H—N(1), H—N(3)). MS (ESI⁺): 180.0 [M+H].

5-(2-Aminoethyl)uracil (31)

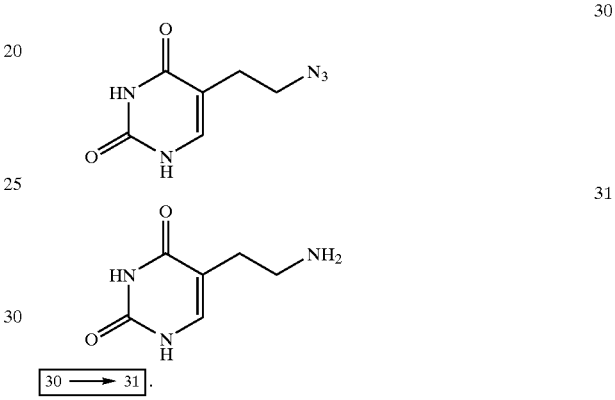

1. Procedure 14.2 g (78.0 mmol) of 30 were suspended in 175 ml of pyridine in a 250 ml three-necked flask equipped with an internal thermometer and reflux condenser and treated with 61.4 g (234 mmol) of triphenylphosphine²⁾. The mixture was heated at 60° C. for five hours and stirred overnight at room temp. (TLC checking, CHCl₃/MeOH 5:1). 40 ml of a 25% strength ammonia solution were added to the solution, which then clarified. The solvents were removed in vacuo in a rotary evaporator. The residue was stirred at room temperature for 30 min in 200 ml of CH₂Cl₂/MeOH 1:1, and the precipitate was filtered off and washed with CH₂Cl₂. After drying in vacuo in a desiccator over phosphorus pentoxide, 10.0 g (85%) of 31 of m.p. 214–220° C. were obtained.

2. Analytical Data 5-(2-Aminoethyl)uracil (31)

M.P.: 214–220° C. and with evolution of gas, presintering. DC: CHCl₃/MeOH/HOAc/H₂O 85:20:10:2, $R_f$ 0.07. UV (MeOH): $\lambda_{max}$ 263.0 (6400). IR (KBr): 3430m, 3109s, 1628s, 1474m, 1394s, 1270s, 1176w, 1103m, 1021m, 966m, 908m, 838m. ¹H-NMR (300 MHz, d₆-DMSO): 2.21 (t, 2H, J(CH₂CH₂N, CH₂CH₂N)=6.8, CH₂CH₂N); 2.59 (t, 2H, J(CH₂CH₂N, CH₂CH₂N) =6.8, CH₂CH₂N); 5.90 (v. br. s, 4H, H—N(1), H—N(3), NH₂); 7.19 (s, H—C(6)). MS (ESI⁻): 153.9 [M–H].

5-(2-Phtalimidoethyl)uracil (32)

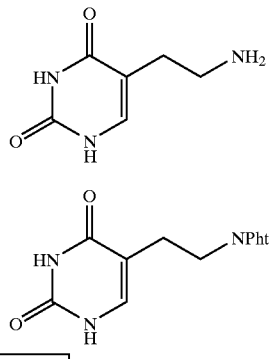

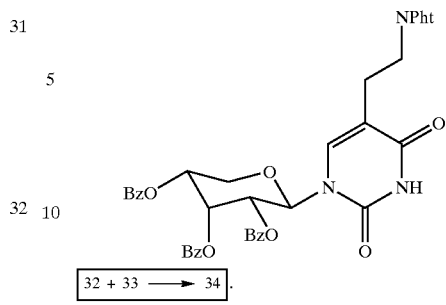

1. Procedure 9.6 g (61.8 mmol) of 31 were suspended in 100 ml of water in a 250 ml round-bottomed flask and treated with 6.64 g (62.6 mmol) of $Na_2CO_3$. After stirring at room temp. for 15 min, 14.3 g (65 mmol) of N-ethoxycarbonylphtalimide were added in portions and the mixture was stirred at room temp. for three hours (TLC checking, $CHCl_3$/MeOH 5:1). The now viscous, white suspension was carefully[1] adjusted to pH 4 using conc. hydrochloric acid and the white precipitate was filtered off. After washing with water, the solid was dried over phosphorus pentoxide in a desiccator in vacuo. This yielded 16.0 g (91%) of 32 of m.p. 324–327° C.

2. Analytical Data

5-(2-Phtalimidoethyl)uracil (32):

M.p.: 324–327° C. with decomp. TLC: $CHCl_3$/MeOH 5:1, $R_f$ 0.51. UV (MeOH): $\lambda_{max}$ 263.0 (5825); $\lambda$298.0 (sh., 1380). IR (KBr): 3446m, 3216m, 1772m, 1721s, 1707s, 1670s, 1390m. $^1$H-NMR (300 MHz, $d_6$-DMSO): 2.49 (t, 2H, J($CH_2CH_2N$, $CH_2CH_2N$)=6.0, $CH_2CH_2N$); 3.71 (t, 2H, J($CH_2CH_2N$, $CH_2CH_2N$)=6.0, $CH_2CH_2N$); 7.24 (s, H—C (6)); 7.84 ($m_c$, 4H, NPht); 10.76 (br. s, H—N(1), H—N(3)). MS (ESF$^-$): 284.0 [M–H].

1-(2, 3, 4-Tri-O-benzoyl-β-D-ribopyranosyl)-5-(2-phtalimidoethyl)uracil (34)

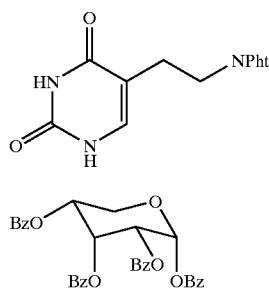

1. Procedure 7.00 g (24 mmol) of 32 and 13.6 g (24 mmol) of 33 were suspended in 120 ml of acetonitrile in a 250 ml three-necked flask, equipped with an argon lead-in, internal thermometer and septum. Firstly 12.2 ml (50 mmol) of BSA and, after stirring for 30 min, a further 7 ml (28 mmol) of BSA were then added by means of syringe. After heating to 40° C. for a short time, the reaction mixture clarified. 13 ml (72 mmol) of TMSOTf were added by means of syringe at room temp. After one hour, no product formation was yet observed (TLC checking, AcOEt/n-heptane 1:1). A further 13 ml (72 mmol) of TMSOTf were therefore added. Subsequently, the reaction mixture was heated to 50° C. After stirring at 50° C. for 2.5 h (TLC checking), the mixture was cooled to RT., [lacuna] onto an ice-cold mixture of 250 ml of AcOEt and 190 ml of satd. $NaHCO_3$ solution and intensively extracted by stirring for 10 min. It was again washed with 100 ml of $NaHCO_3$ solution and the aqueous phases were again extracted with 100 ml of AcOEt. The dil. org. phases were dried using $MgSO_4$ and the solvents were removed in vacuo in a rotary evaporator. After drying in an oil pump vacuum, 20.9 g of crude product were obtained. Chromatography on silica gel (h=25 cm, f=5 cm, AcOEt/n-heptane 1:1) yielded a TLC-uniform, foamy product, which was digested using $Et_2O$. Filtration and drying in an oil pump vacuum afforded 15 g (86%) of 34.

2. Analytical Data

1-(2, 3, 4-Tri-O-benzoyl-β-D-ribopyranosyl)-5-(2-phtalimidoethyl)uracil (34)

M.p.: 124° C. (sintering). TLC: AcOEt/n-heptane 1:1, $R_f$ 0.09. UV (MeOH): $\lambda_{max}$ 263.0 (11085); $\lambda$299.0 (sh., 1530). IR (KBr): 3238w, 3067w, 1772m, 1710s, 1452m, 1395m, 1266s, 1110s, 1070m, 1026m. $^1$H-NMR (300 MHz, $CDCl_3$): 2.79 ($m_c$, 2H, $CH_2CH_2N$); 3.96 ($m_c$, 2H, $CH_2CH_2N$); 4.06 (dd, J($H_{eq}$—C(5'), $H_{ax}$—C(5'))=11.0, J($H_{eq}$—C(5'), H—C(4'))=6.0, $H_{eq}$—C(5')); 4.12 (t, J($H_{ax}$—C(5'), $H_{eq}$—C(5'))= J($H_{ax}$—C(5'), H—C(4')) =11.0, $H_{ax}$—C(5')); 5.39 (dd, J(H—C(2'), H—C(1'))=9.5, J(H—C(2'), H—C(3'))=2.9, H—C(2')); 5.46 (ddd, J(H—C(4'), $H_{ax}$—C(5'))=11.0, J(H—C(4'), $H_{eq}$—C(5'))=6.0, J(H—C(4'), H—C(3'))=2.9, H—C(4')); 6.26 (ψt, J≈2.6, H—C(3')); 6.36 (d, J(H—C(1'), H—C(2'))=9.5, H—C(1')); 7.24–7.40, 7.44–7.56, 7.61–7.66, 7.72–7.80, 7.84–7.90, 8.06–8.13 (6m, 16H, 3 Ph, H—C(6)); 7.70, 7.82 (2 $m_c$, 4H, NPht); 8.37 (s, H—N(3)). $^{13}$C-NMR (75 MHz, $CDCl_3$): 21.19 ($CH_2CH_2N$); 36.33 ($CH_2CH_2N$); 64.07 (C(5')); 66.81, 68.22 (C(4'), C(2')); 69.29 (C(3')); 78.59 (C(1')); 112.42 (C(5)); 123.31, 132.05, 133.89 (6C, Pht); 128.33, 128.47, 128.47, 128.83, 128.86, 129.31, 129.83, 129.83, 129.94, 133.55, 133.62, 133.69 (18C, 3 Ph); 135.87 (C(6)); 150.39 (C(2)); 162.78 (C(4)); 164.64, 165.01, 165.41 (3C, $O_2$CPh); 168.43 (2C, CO-Pht). MS (ESI$^+$):

730.2 [M+H]. Anal.: calc. for $C_{40}H_{31}N_3O_{11}$ (729.70): C 65.84, H 4.28, N 5.76; found: C 65.63, H 4.46, N 5.53.

5-(2-Phtalimidoethyl)-1-(β-D-ribopyranosyl)uracil (35)

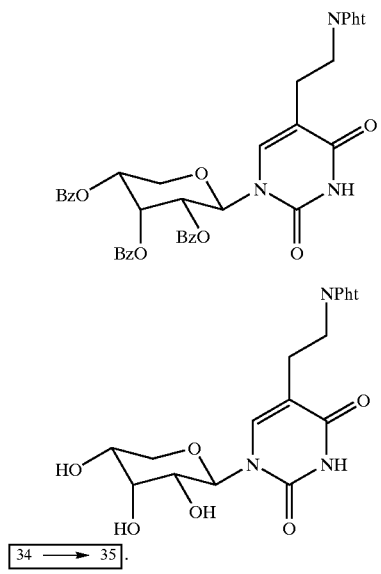

1. Procedure 15 g (20 mmol) of 34 were dissolved in 500 ml of MeOH in a 1 l round-bottomed flask, treated with 324 mg (6 mmol) of NaOMe and stirred at room-temp. overnight with exclusion of water (TLC checking, AcOEt/n-heptane 1:1). Amberlite IR-120 was added to the resulting suspension until the pH was <7. The solid was dissolved in the presence of heat, filtered off hot from the ion exchanger and washed with MeOH. After removing the solvent, the residue was co-evaporated twice using 150 ml of water each time. This yielded 9 g of crude product, which was heated under reflux in 90 ml of MeOH for 10 min. After cooling to room temp., the mixture was treated with 60 ml of $Et_2O$ and stored overnight at 4° C. Filtration, washing with $Et_2O$ and drying in an oil pump vacuum yielded 7.8 g (93%) of 35.

2. Analytical Data

5-(2-Phtalimidoethyl)-1-(β-D-ribopyranosyl)uracil (35)

M.p.: 137° C. (sintering). TLC: $CHCl_3$/MeOH 5:1, $R_f$ 0.21. UV (MeOH): $\lambda_{max}$ 263.0 (8575); λ.299.0 (sh., 1545). IR (KBr): 3458s, 1772w, 1706s, 1400m, 1364m, 1304m, 1045m. $^1$H-NMR (300 MHz, $d_6$-DMSO+2 Tr. $D_2O$): 2.55 ($m_c$, 2H, $CH_2CH_2N$); 3.28–3.61 (m, 4H, H—C(2'), H—C(4'), $H_{eq}$—C(5'), $H_{ax}$—C(5')); 3.73 ($m_c$, 2H, $CH_2CH_2N$); 3.93 (m, H—C(3')); 5.50 (d, J(H—C(1'), H—C(2'))=9.3, H—C(1')); 7.41 (s, H—C(6)); 7.84 (s, 4H, NPht). $^{13}$C-NMR (75 MHz, $d_6$-DMSO): 25.63 ($CH_2CH_2N$); 36.62 ($CH_2CH_2N$); 64.95 (C(5')); 66.29 (C(4')); 67.37 (C(2')); 71.12 (C(3')); 79.34 (C(1')); 110.39 (C(5)); 122.85, 131.54, 134.08 (6C, Pht); 137.92 (C(6)); 150.84 (C(2)); 163.18 (C(4)); 167.74 (2C, CO-Pht). MS (ESI$^-$) 416.1 [M–H].

1-(2'-O-Benzoyl-β-D-ribopyranosyl)-5-(2-phtalimidoethyl)uracil 10.6 g (0.025 mmol) of 5-(2-phtalimidoethyl)-1-(β-D-ribopyranosyl)uracil were dissolved in 20 ml of pyridine in a heated and argon-flushed 1 l four-necked flask and mixed with 200 ml of dichloromethane. The mixture was cooled to −70° C., 3.82 ml (0.033 mmol) of benzoyl chloride in 5 ml of pyridine and 20 ml of dichloromethane were slowly added dropwise with cooling and the mixture was stirred at −70° C. for 35 min. The reaction mixture was poured onto 600 ml of cooled ammonium chloride solution and the aqueous phase was extracted with ethyl acetate. The combined organic phases were washed with water, dried and concentrated to dryness in vacuo. Chromatography on silica gel (ethyl acetate/heptane 1:1) yielded 7.9 g (60%) of 1-(2'-O-benzoyl-β-D-ribopyranosyl)-5-(2-phtalimidoethyl) uracil.

TLC: $R_f$ 0.24 (ethyl acetate/heptane 4:1). $^1$H-NMR (300 Mhz, $d_6$-DMSO): 2.67 ($m_c$, 2H, $CH_2CH_2N$); 3.66–5 3.98 (m, 5H, H—C(4'), $H_{eq}$—C(5'), $H_{ax}$—C(5'), $CH_2CH_2N$); 4.51 (t, 1H, H—C(3')); 4.98 (dd, 1H, H—C(2')); 6.12 (d, 1H, H—C(1')); 7.19 (s, 1H, H—C(6)); 7.29–7.92 (m, 9H, OBz, NPht).

1-(2-O-Benzoyl-4O-(4,4'-dimethoxytrityl)-β-D-ribopyranosyl)-5-(2-phtalimidoethyl)uracil 5.6 g (10.73 mmol) of 1-(2-O-benzoyl-β-D-ribopyranosyl-5-(2-phtalimido-ethyl)uracil were dissolved in 60 ml of dichloromethane, treated with 4.72 g (13.95 mmol) of 4,4'-dimethoxytrityl chloride and 2.4 ml (13.95 mmol) of N-ethyldiisopropylamine and stirred at RT for 20 min. The reaction mixture was diluted with 100 ml of dichloromethane, washed with sodium hydrogencarbonate solution and 20% citric acid solution, dried and concentrated to dryness in vacuo. Chromatography on silica gel (ethyl acetate/heptane 1:1 2% triethylamine) yielded 7.7 g (87%) of 1-(2-O-benzoyl-4-O-(4,4'-dimethoxytrityl)-β-D-ribopyransoyl)-5-(2-phtalimidoethyl)uracil.

TLC: $R_f$ 0.53 (ethyl acetate/heptane 1:1+2% triethylamine). $^1$H-NMR (300 MHz, $CDCl_3$): 2.64 ($m_c$, 2H, $CH_2CH_2N$); 3.12 (m, 1H, H—C(4')); 3.59–3.63 and 3.72–3.92 (m, 5H, H—C(3'), $H_{eq}$—C(5'), $H_{ax}$—C(5'), $CH_2CH_2N$); 3.81 and 3.82 (s, 6H, $CH_3O$); 4.70 (dd, 1H, H—C(2')); 6.09 (d, 1H, H—C(1')); 7.05 (s, 1H, H—C(6)); 6.84–7.90 (m, 22H, ODmt, OBz, NPht).

1-(3-O-Benzoyl-4-O-(4,4'-dimethoxytrityl)-β-D-ribopyranosyl) 5-(2-phtalimidoethyl)uracil 3 g (3.63 mmol) of 1-(2-O-Benzoyl-4-O-(4,4'-dimethoxytrityl)-β-D-ribopyranosyl)-5-(2-phtalimidoethyl) uracil, 1 g (7.26 mmol) of 4-nitrophenol, 0.44 g (3.63 mmol) of 4-(dimethylamino)pyridine and 3.75 ml (21.78 mmol) of N-ethyldiisopropylamine were dissolved in 5.6 ml of isopropanol and 25 ml of pyridine, heated to 65° C. and stirred at 65° C. for 3 days. The solution was concentrated to dryness in vacuo and the residue was dissolved in 150 ml of dichloromethane. After washing with 20% citric acid solution and sodium hydrogencarbonate solution, the solution was dried over magnesium sulphate. Chromatography on silica gel (ethyl acetate/dichloromethane/isohexane 2:1:1) yielded 2.27 g (76%) of 1-(3-O-benzoyl-4-O-(4,4'-dimethoxytrityl)-β-D-ribopyranosyl)-5-(2-phtalimidoethyl)uracil.

TLC: $R_f$ 0.27 (ethyl acetate/isohexane 2:1+1% triethylamine). $^1$H-NMR (300 MHz, $CDCl_3$): 2.39 ($m_c$, 2H, $CH_2CH_2N$); 2.53 ($m_c$, 1H, $H_{eq}$—C(5')); 3.30 (dd, 1H, H—C(2')); 3.55 ($m_c$, 1H, $H_{ax}$—C(5')); 3.69 ($m_c$, 2H, $CH_2CH_2N$); 3.78 and 3.79 (s, 6H, $CH_3O$); 3.79–3.87 (m, 1H, H—C(4')); 5.74 (d, 1H, H—C(1')); 5.77 ($m_c$, 1H, H—C(3')); 6.92 (s, 1H, H—C(6)); 6.74–8.20 (m, 22H, ODmt, OBz, NPht).

1-{2'-O-[(Allyloxy)(diisopropylamino)phosphino]-3'-O-benzoyl-4'-O-[(4,4'-dimethoxytriphenyl)methyl]-β-D-ribopyranosyl}-5-(2-phtalimidoethyl)uracil 88 mg (0.11 mmol) of 1-(3-O-benzoyl-4-O-(4,4'-dimethoxytrityl)-β-D-ribopyranosyl)-5-(2-phtalimidoethyl)uracil were dissolved in 5 ml of dichloromethane, treated with 75 μl (0.44 mmol) of N-ethyldiisopropylamine and 70 μl (0.3 mmol) of allyloxychloro(diisopropylamino)phosphine and stirred for 3 h at room temperature. After addition of a further 35 μl (0.15 mmol) of allyloxychloro(diisopropylamino)phosphine to complete the reaction, it was stirred for a further 1 h at room temperature and the reaction mixture was concentrated in vacuo. Chromatography on silica gel (ethyl acetate/heptane: gradient 1:2 to 1:1 to 2:1, in each case with 2% triethylamine) yielded 85 mg (76%) of 1-{2'-O-[(allyloxy)(diisopropylamino)phosphino]-3'-O-benzoyl-4'-O-[(4,4'-dimethoxy-triphenyl)methyl]-β-D-ribopyranosyl}-5-(2-phtalimidoethyl)uracil.

TLC: $R_f$ 0.36 (ethyl acetate/heptane 2:1). $^1$H-NMR (CDCl$_3$, 300 MHz,): selected characteristic positions: 2.28, 2.52 (2 dd, J=5.0, 11.0 Hz, 2 H, 2 H-5'), 3.79, 3.78 (app. 2 s, 12 H, OMe), 6.14 (1 bs, 1 H, H-3'). $^{31}$P-NMR(CDCl$_3$): 149.8, 150.6.

Example 2

Indole-based Linker

N-phthaloyltryptamine is obtained from phthalic anhydride and tryptamine as described (Kuehne et al J. Org. Chem. 43, 13, 1978, 2733–2735). This is reduced with borane-THF to give the indoline (analogously to A. Giannis, et al., Angew. Chem. 1989, 101, 220).

The 3-substituted indoline is first reacted with ribose to give the nucleoside triol and then with acetic anhydride to give the triacetate. The mixture is oxidized with 2,3-dichloro-5,6-dicyanoparaquinone and the acetates are cleaved with sodium methoxide, benzoylated selectively in the 2'-position, DM-tritylated selectively in the 4'-position, and the migration reaction is carried out to give the 3'-benzoate. The formation of the phosphoramidite is carried out in the customary manner. This can be employed for the automated oligonucleotide synthesis without alteration of the synthesis protocols.

Procedure 3-(N-Phthaloyl-2-aminoethyl)indoline

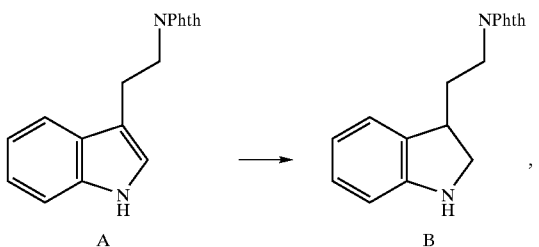

51.4 g (177 mmol) of phthaloyltryptamine A were dissolved in 354 ml of 1 M borane-THF solution (2 eq.) under a nitrogen atmosphere and cooled to 0° C. 354 ml of trifluoroacetic acid were slowly added dropwise at 0° C. (caution: evolution of gas) and the mixture was stirred for 30 min. (TLC checking: EtOAc). 17.3 ml of water were then added, and the mixture was stirred for 10 min and concentrated in vacuo. The residue was dissolved in 10% strength NaOH solution/dichloromethane, and the organic phase was separated off, dried over NaSO$_4$, filtered and concentrated in vacuo. The residue [50.9 g] was recrystallized from hot ethanol (3 l). 41.4 g of B were obtained, m.p. 161–162° C. The mother liquor was concentrated in vacuo and the residue was again recrystallized from ethanol. A further 3.2 g of B were obtained, m.p. 158–159° C.

Total yield: 44.6 g (153 mmol) of B, i.e. 86%. $^1$H-NMR (CDCl$_3$, 300 MHz): 1.85–2.00, 2.14–2.28 (2 m, 2×1 H, CH$_2$CH$_2$NPhth), 2.70 (bs, 1 H, NH), 3.24–3.38, 3.66–3.86 (2 m, 5 H, CH$_2$CH$_2$NPhth, H-2a, H-2b, H-3), 6.62 (d, J=8.0 Hz, 1 H, H-7), 6.66–6.72 (m, 1 H, H-5), 6.99 (app t, J=7.5 Hz, 1 H, H-6), 7.14 (d, J=8.0 Hz, 1 H, H-4), 7.64–7.74, 7.78–7.86 (2 m, 2×2 H, Phth). $^{13}$C-NMR (CDCl$_3$, 75 MHz): 32.70, 36.10 (2 t, C-2, CH$_2$CH$_2$NPhth), 39.62 (d, C-3), 53.04 (t, CH$_2$NPhth), 109.65 (d, C-7), 118.74 (d, C-5), 123.25 (d, Phth), 123.92, 127.72 (2 d, C-4, C-6), 131.81 (s, C-3a), 132.14 (s, Phth), 133.99 (d, Phth), 151.26 (s, C-7a), 168.38 (s, C=O). Calc.: C: 73.96, H: 5.52, N: 9.58; found: C: 73.89, H: 5.57, N: 9.55. MS (ES$^+$): 293 (MH$^+$, 100%), 3-(N-Phthaloyl-2-aminoethyl)-1-(2',3',4'-tri-O-acetyl-β-D-ribopyranosyl)indole

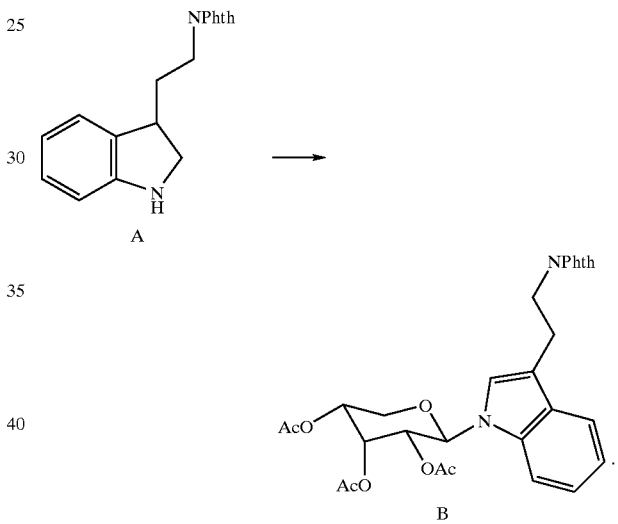

45.2 g (155 mmol) of A and 23.2 g (155 mmol; 1.0 eq.) of D-ribose were suspended in 750 ml of dry ethanol and heated to reflux for 4 h under a nitrogen atmosphere (TLC checking: CH$_2$Cl$_2$/MeOH 10:1). After cooling to RT, the mixture was concentrated in vacuo. The residue was dissolved in 300 ml of pyridine and treated with 155 ml of acetic anhydride with ice-cooling. After 15 min., the ice bath was removed and the mixture was stirred at RT for 18 h (TLC checking: EtOAc/isohexane 1:1). This solution was concentrated in vacuo and co-evaporated three times with 300 ml of toluene each time. The oil obtained is dissolved in 900 ml of dichloromethane and treated with 38.8 g (171 mmol; 1.1 eq.) of 2,3-dichloro-5,6-dicyanoparaquinone with ice-cooling. After 15 min., the ice bath was removed and the mixture was stirred at RT for 1.5 h (TLC checking: EtOAc/isohexane 1:1). The deposited precipitate was filtered off with suction and washed with dichloromethane and discarded. The filtrate was washed with 600 ml of satd. NaHCO$_3$ solution. The precipitate deposited in the course of this was again filtered off with suction and washed with dichloromethane and discarded. The combined organic extracts were dried over Na$_2$SO$_4$ and concentrated in vacuo.

The residue (90.9 g) was purified by flash chromatography on silica gel 60 (10×25 cm; EtOAc/isohexane 2:3).

The following were obtained: 21.5 g of pure B and 46.83 g of mixed fractions, which after fresh chromatography yielded a further 20.4 g of pure B. Total yield: 41.9 g (76 mmol) of B, i.e. 49%. $^1$H-NMR (CDCl$_3$, 300 MHz): 1.64, 1.98, 2.19 (3 s, 3×3 H, Ac), 3.06 (t, J=8.0 Hz, 2 H, C$\underline{H}_2$CH$_2$NPhth), 3.81–4.00 (m, 4 H, H-5'ax, H-5'eq, C$\underline{H}_2$NPhth), 5.13 (ddd, J=2.5, 6.0, 10.5 Hz, 1 H, H-4'), 5.36(dd, J =3.5, 9.5 Hz, 1 H, H-2'), 5.71 (d, J=9.5 Hz, 1 H, H-1'), 5.74(app t, J=3.0 Hz, 1 H, H-3'), 7.02(s, 1 H, H-2), 7.04–7.10, 7.13–7.19 (2 m, 2×1 H, H-5, H-6), 7.33 (d, J=8.0 Hz, 1 H, H-7), 7.5.58–7.66, 7.72–7.80(2 m, 5 H, Phth, H-4). $^{13}$C-NMR (CDCl$_3$, 75 MHz): 20.23, 20.65, 20.87 (3 q, Ac), 24.41, 38.28 (2 t, CH$_2$CH$_2$), 63.53 (t, C-5'), 66.24, 68.00, 68.64 (3 d, C-2', C-3', C-4'), 80.33 (d, C-1'), 109.79 (d, C-7), 113.95 (s, C-3), 119.33, 120.39, 122.04, 122.47 (4 d, C-4, C-5, C-6, C-7), 123.18 (d, Phth), 128.70, 132.17 (2 s, C-3a, Phth), 133.87 (d, Phth), 136.78 (s, C-7a), 168.243, 168.77, 169.44, 169.87 (4 s, C=O). Calc.: C: 63.50, H: 5.15, N: 5.11; found: C: 63.48, H: 5.16, N: 5.05. MS (ES$^+$): 566 (M+NH$_4^+$, 82%), 549 (MH$^+$, 74%), 114 (100%).

3-(N-Phthaloyl-2-aminoethyl)-1-β-D-ribopyranosylindole

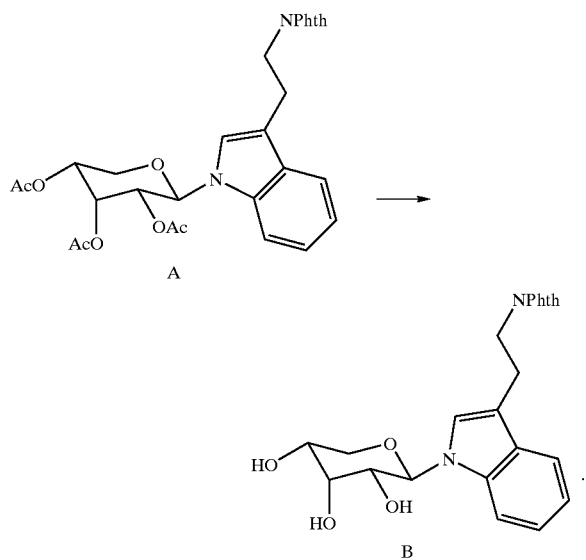

44.1 g (80 mmol) of A were dissolved in 400 ml of anhydrous methanol under a nitrogen atmosphere. The mixture was treated with 4.0 ml of 30% strength sodium methoxide solution with ice-cooling and then stirred for 18 h at RT. The deposited precipitate was filtered off with suction and washed with cold ethanol. The filtrate was concentrated in vacuo. The residue was taken up in dichloromethane. This solution was washed with satd. NaHCO$_3$ solution, dried over NaSO$_4$ and concentrated in vacuo. The residue obtained was recrystallized from hot ethanol together with the precipitate deposited from the reaction solution. 22.6 g of B were obtained, m.p. 196–198° C. The mother liquor was concentrated in vacuo and the residue was again recrystallized from ethanol. A further 9.2 g of B were obtained, m.p. 188–194° C.

Total yield: 25.8 g of B, i.e. 76%. $^1$H=NMR (MeOD, 300 MHz): 3.09 (app. t, J=7.0 Hz, 2 H, C$\underline{H}_2$CH$_2$NPhth), 3.64–3.98 (m, 5 H, H-4', H-5'ax, H-5'eq, C$\underline{H}_2$NPhth), 4.05 (dd, J=3.5, 9.5 Hz, 1 H, H-2'), 4.22 (app t, J=3.0 Hz, 1 H, H-3'), 5.65 (d, J=9.5 Hz, 1 H, H-1'), 6.95–7.05, 7.09–7.16 (2 m, 2×1 H, H-5, H-6), 7.25 (s, 1 H, H-2), 7.44 (d, J=80 Hz, 1 H, H-7), 7.60 (d, J=8.0 Hz, 1 H, H-4), 7.74–7.84 (m, 4 H, Phth). $^{13}$C-NMR (d$_6$-DMSO, 75 MHz): 23.87, 37.79 (2 t, C$\underline{H}_2$CH$_2$NPhth), 64.82 (t, C-5'), 66.74 (d, C-4'), 68.41 (d, C-2'), 71.42 (d, C-3'), 81.37 (d, C-1'), 110.42 (d, C-7), 111.05 (s, C-3), 118.17, 119.21, 121.36, 122.92, 123.80 (5 d, C-2, C-4, C-5, C-6, NPhth), 127.86, 131.59 (2 s, C-3a, Phth), 134.27 (d, Phth), 136.62 (s, C-7a), 167.72 (s, C=O). MS(ES$^-$): 457 (M+OH$^-$+H$_2$O, 49%), 439 (M+OH$^-$, 100%), 421 (M–H$^+$, 28%)

1-(2'-O-Benzoyl-β-D-ribopyranosyl)-3-(N-phthaloyl-2-aminoethyl)indole

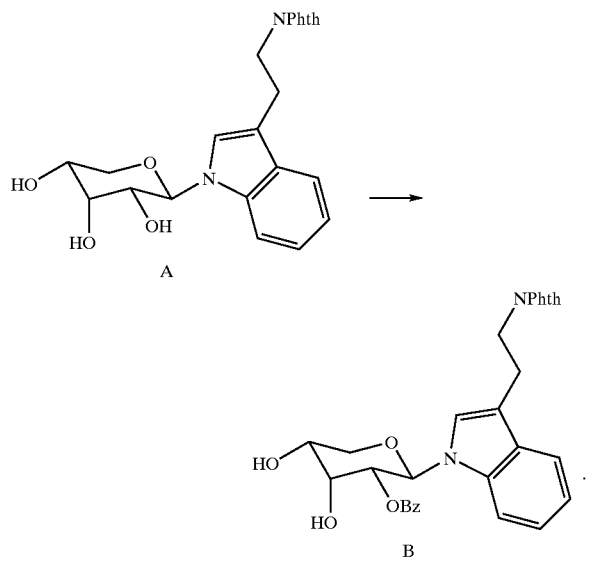

10.6 g (25 mmol) of A was taken up in 250 ml of dry dichloromethane under a nitrogen atmosphere. The mixture was treated with 305 mg of DMAP (2.5 mmol) and 20 ml of pyridine. It was heated until everything was in solution and then cooled to −78° C. 3.35 ml of benzoyl chloride (28.8 mmol) dissolved in 8 ml of dichloromethane were now added dropwise in the course of 15 min. TLC checking (EtOAc/hexane 3:1) after a further 30 min indicated complete reaction. After 45 min, the cold solution was added directly to 200 ml of satd. NH$_4$Cl solution through a folded filter and the filter residue was washed with dichloromethane. The organic phase was washed once with water, dried over MgSO$_4$ and concentrated.

The residue was co-evaporated twice with toluene and purified by flash chromatography on 10×20 cm silica gel using EtOAc/hexane 3:1. 8.1 g of B (64%) were obtained. $^1$H-NMR (CDCl$_3$, 300 MHz): 2.45, 2.70 (2 bs, 2×1 H, OH), 3.04 (t, J=8.0 Hz, 2 H, C$\underline{H}_2$CH$_2$NPhth), 3.80–4.20 (m, 5 H, H-4', H-5'ax, H-5'eq, C$\underline{H}_2$NPhth), 4.63 (bs, 1 H, H-3'), 5.46 (dd, J=3.5, 9.5 Hz, 1 H, H-2'), 6.03 (d, J=9.5 Hz, 1 H, H-1'), 7.08–7.31 (m, 5 H, H-2, H-5, H-6, Bz-m-H), 7.41–7.48 (m, 1 H, H-Bz-p-H), 7.50 (d, J=8.0 Hz, 1 H, H-7), 7.64–7.79 (m, 7 H, Phth, H-4, Bz-o-H). $^{13}$C-NMR (d$_6$-DMSO, 75 MHz): 24.40, 38.22 (2 t, CH$_2$C$\underline{H}_2$NPhth), 65.95 (t, C-5'), 66.65 (d, C-4'), 69.55 (d, C-3'), 71.87 (d, C-2'), 79.57 (d, C-1'), 109.96 (d, C-7), 113.70 (s, C-3), 119.21, 120.21, 122.11, 122.41, 123.14, (5 d, C-2, C-4, C-5, C-6, NPhth), 128.28 (d, Bz), 128.58, 128.59, (2 s, C-3a, Bz), 129.62 (d, Phth), 132.05 (s, Phth), 133.81 (Bz), 136.97 (s, C-7a), 165.12, 168.29 (2 s, C=O). MS(ES$^-$): 525 (M–H$^+$, 12%), 421 (M–PhCO$^+$, 23%), 107 (100%).

1-3'-OBenzoyl-4'O-[(4,4'-dimethoxytriphenyl)methyl]-β-D-ribopyranosyl-3-(N-phthanloyl-2-aminoethyl)indole

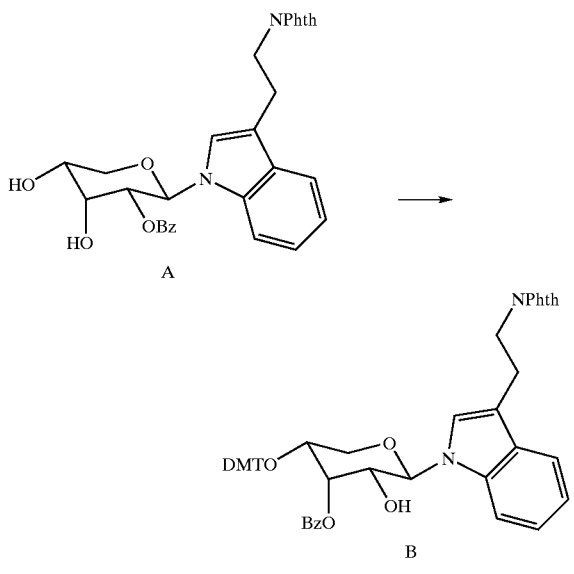

8.9 g (16.9 mmol) of A was suspended in 135 ml of dry dichloromethane under a nitrogen atmosphere. The mixture was treated with 206 mg of DMAP (1.68 mmol), 5.8 ml of N-ethyldiisopropylamine (33.7 mmol) and about 12 ml of pyridine (until solution was complete). It was now treated with 34 g of molecular sieve 4 Å and stirred for 30 min. After cooling to 0° C., it was treated with 11.4 g of DMTCl (33.7 mmol) and stirred for 75 min after removing the cooling bath. A further 1.94 g (0.34 eq) and, after a further 40 min, 1.14 g (0.2 eq) and, after a further 65 min, 1.14 g of DMTCl (0.2 eq) were then added. After 4.25 h the reaction was complete. The mixture was then treated with 25.3 ml of n-propanol (20 eq), stirred for a further 30 min and then concentrated cautiously (foam formation). The residue was dissolved in 100 ml of pyridine. It was treated with 1.85 g of DMAP (15.1 mmol; 0.9 eq), 13.05 ml of N-ethyldiisopropylamine (101 mmol; 6.0 eq), 71 ml of n-propanol (940 mmol; 56 eq) and 3.74 g of p-nitrophenol (26.9 mmol; 1.6 eq). This mixture was stirred under nitrogen for 96 h at 75–80° C. After cooling to room temperature, the mixture was filtered through Celite and concentrated. The residue was purified by flash chromatography on 9×17 cm silica gel using toluene/diethyl ether/triethylamine 90:10:1. The product-containing fractions (9.25 g) were first recrystallized from EtOAc and then reprecipitated from toluene/methanol. 5.86 g of B (42%) were obtained.

$^1$H-NMR (CDCl$_3$, 300 MHz): 2.64 (bs, 1 H, OH), 2.68 (dd, J=5.0, 11.5 Hz, 1 H, H-5'eq), 2.94 (dd, J=7.5, 16.0 Hz, 1 H, CHCH$_2$NPhth), 3.03 (dd, J=8.0, 16.0 Hz, 1 H, CH$_2$CH$_2$NPhth), 3.67–3.74 (m, 1 H, H-5'ax), 3.69, 3.70 (2 s, 2×3 H OMe), 3.85 (t, J=7.5 Hz, 2H, CH$_2$CH$_2$NPhth), 3.94 (ddd, J=3.0, 5.0, 10.5 Hz, 1 H, H-4'), 4.03 (dd, J=3.5, 9.0 Hz, 1 H, H-2'), 5.51 (d, J=9.0 Hz, 1 H, H-1'), 5.86 (bs, 1 H, H-3'), 6.68–7.66 (m, 25 H), 8.19–8.30 (m, 2 H). $^{13}$C-NMR (CDCl$_3$, 75 MHz): 24.16, 38.80 (2 t, CH$_2$CH$_2$NPhth), 55.25, 55.26 (2 q, Ome), 65.58 (t, C-5'), 68.29, 69.19, 73.83 (3 d, C-2', C-3', C-4'), 83.03 (d, C-1'), 87.31 (CAr$_3$)110.03 (d, C-7), 113.37, 113.47 (2 d), 113.53 (s, C-3), 118.95, 120.20, 122.28, 122.31, 123.10, 127.07, 128.02, 128.08, 128.68 (9 d), 128.74 (s), 130.02, 130.19, 130.22 (3 d), 130.37, 131.95 (2 s), 133.40, 133.83 (2 d), 135.98, 136.14, 136.56, 145.12, 158.82, 166.76, 168.52 (7 s, C-7a, 2 COMe, 2 C=O).

1-'O-(Allyloxy)(diisopropylamino)phosphino)-3'-O-Benzoyl-4'O-[(4,4'- dimethoxytriphenyl)methyl]-β-D-ribopyranosyl-3-(N-phthaloyl-2-aminoethyl)indole (2 diastereomers)

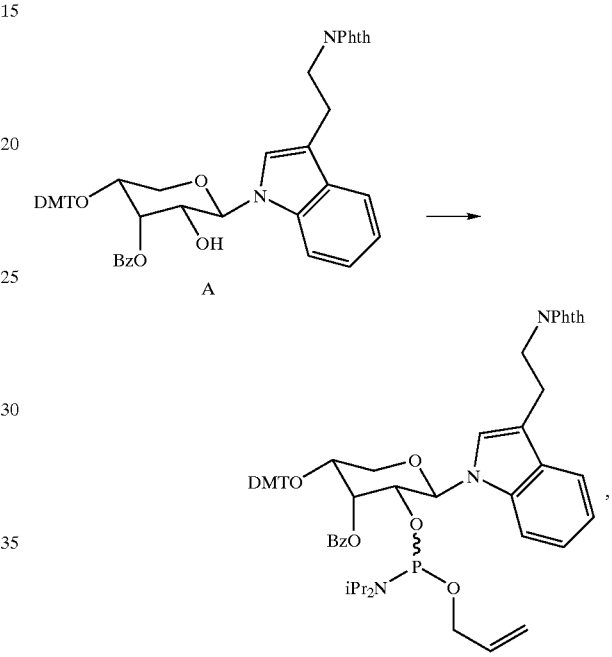

1658 mg of alcohol A (2.0 mmol) was dissolved in 10 ml of dry dichloromethane under an argon atmosphere. The solution was treated with 1.03 ml of N-ethyldiisopropylamine (6.0 mmol) and 0.63 ml of monoallyl n-diisopropylchlorophosphoramidite (2.8 mmol) and stirred for 1 h at room temperature. The excess phosphorylation reagent was then destroyed by addition of 61 μl (0.8 mmol) of isopropanol. After 10 min, the mixture was concentrated in vacuo and the residue was purified by flash chromatography on 3.3×21 cm silica gel using hexane/EtOAc/NEt$_3$ (75:25:1). The product-containing fractions were concentrated, taken up in CCl$_4$ and concentrated again. 2.04 g of an almost colourless foam (quant.) were obtained, which can be used thus directly for oligomerization and can be kept at −20° C. for a number of weeks.

TLC on silica gel (EtOAc/hexane/NEt$_3$ 33:66:1): 0.41
$^1$H-NMR (CDCl$_3$, 300 MHz): selected characteristic positions: 2.42, 2.53, (2 dd, J=5.0, 11.0 Hz, 2 H, 2 H-5'eq), 3.76, 3.77, 3.78, 3.79 (4 s, 4×3 H, OMe), 5.70, 5.73 (2 d, J=9.0 Hz, 2 H, 2 H-1'), 6.16, 6.29 (2 bs, 2 H, 2 H-3'). $^{31}$P-NMR (CDCl$_3$): 150.6, 151.0

Example 3

Lysine-based Linker

The synthesis is depicted in Scheme 4 and is described in detail below.

Scheme 4: Synthesis of the lysine linker

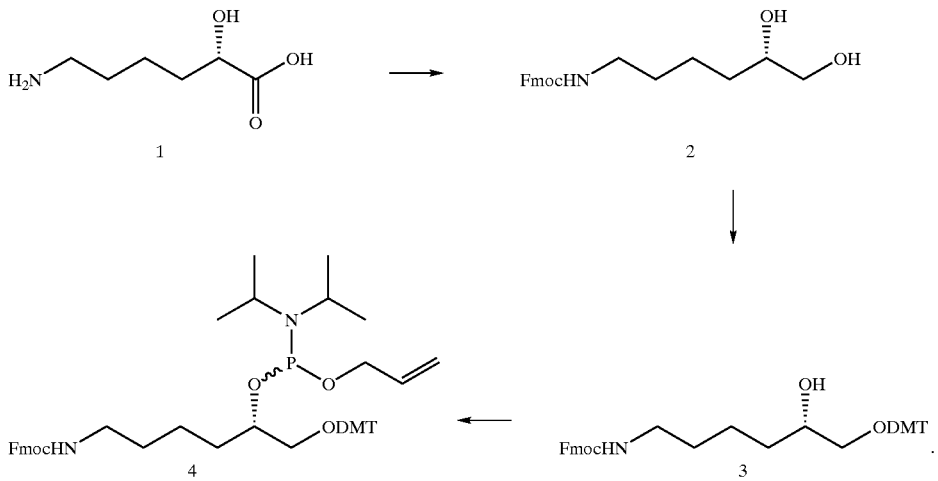

6-Amino-2(S)-hydroxyhexanoic acid (1) was prepared from L-lysine in a manner known from the literature by diazotization and subsequent hydrolysis (K.-I. Aketa, Chem. Pharm Bull. 1976, 24, 621).

2-(S)-N-Fmoc-6-amino-1,2-hexanediol (2)

3.4 g of LiBH$_4$ (156 mmol, 4 eq) are dissolved under argon in 100 ml of abs. THF (exothermic!). After cooling to about 30° C., 39.6 ml of TMSCl (312 mmol, 8 eq) are slowly added dropwise (evolution of gas!), a precipitate being formed. 5.74 g of 6-amino-2(S)-hydroxyhexanoic acid (1) (39 mmol) are added in portions. in an argon countercurrent and the mixture is heated to 65° C. until the TLC (silica gel; i-PrOH/conc. NH$_4$OH/water 7:2:1; staining with ninhydrin) no longer shows any starting material (about 3 h). The mixture is cautiously treated with 120 ml of methanol with ice-cooling (strong evolution of gas!). The solvent is concentrated in vacuo, and the residue is co-evaporated three times with 200 ml of methanol each time and then dissolved in 100 ml of abs. DMF. After addition of 16 ml of ethyldiisopropylamine (93.6 mmol, 2.4 eq), the mixture is cooled to 0C and treated in portions with 12.1 g of FmocCl (46.8 mmol, 1.2 eq). After 15 minutes, the cooling bath is removed and the mixture is stirred at room temperature until the starting material has been consumed (about 3 h; TLC checking: silica gel; CHCl$_3$/MeOH/HOAc/water 60:30:3:5). The reaction solution is added to 600 ml of satd. NaHCO$_3$ solution. The precipitate is filtered off, washed with 200 ml of water and dried at 50° C. in a high vacuum until the weight is constant (about 6 h). 13.9 g of a colourless solid is obtained, which is recrystallized from ethyl acetate (40 ml)/n-hexane (35 ml). Yield: 9.05 g (65%).

$^1$H-NMR (300 MHz, CDCl$_3$): 7.68, 7.51 (2 d, J=8.0 Hz, in each case 2 H, Ar—H), 7.32 (t, J=8.0 Hz, 2 H, Ar—H), 7.23 (dt, J=1.6, 8.0 Hz, 2 H, Ar—H), 4.92 (bs, 1 H. NH), 4.32 (d, J=7.0 Hz, 2 H, OCOCH$_2$), 4.13 (bt, J=7.0 Hz, OCOCH$_2$CH), 3.64–3.58 (m, 1 H, H-1, H-1', H-2, H-6, H-6'), 3.54 (dd, J=3.2, 11.0Hz, 1 H, H-1, H-1', H-2, H-6, H-6'), 3.35 (dd, J=7.4, 11.0 Hz, 1 H, H-1, H-1', H-2, H-6, H-6'), 3.16–3.06 (m, 2 H, H-1, H-1', H-2, H-6, H-6'), 3.0–2.0 (bs, 2 H, OH), 1.52–1.18 (m, 6 H, H-3, H-3', H-4, H-4', H-5, H-5').

2-(S)-N-Fmoc-O$^1$-DMT-6-amino-1,2-hexanediol (3) was DM-tritylated according to WO 89/02439.

2-(S)-N-Fmoc-O$^1$-DMT-O$^2$-allyloxydiisopropylaminophosphinyl-6-amino-1,2-hexanediol (4)

0.51 ml of ethyldiisopropylamine (3.0 mmol, 3 eq) and 0.33 ml of chloro-N,N-diisopropylaminoallyloxyphosphine (1.5 mmol, 1.5 eq) are added under argon to a solution of 670 mg of the alcohol (3) (1.02 mmol) in 10 ml of abs. dichloromethane. The mixture is stirred at room temperature for 2 h, the solvent is stripped off in vacuo and the residue obtained is purified by flash chromatography on 3.2×16 cm silica gel (EtOAc/isohexane/NEt$_3$ 20:80:1). 839 mg (97%) of a slightly yellowish oil are obtained.

TLC: silica gel; EtOAc/isohexane/NEt$_3$ 50:50: 1; UV; R$_f$=0.77. $^1$H=NMR (300 MHz, CDCl$_3$): 7.70–6.68 (m, 21 H, Ar—H), 4.92–4.62 (m, 1 H. NH), 4.31 (d, J=7.0 Hz, 2 H, OCOCH$_2$), 4.13 (t, J=7.0 Hz, 1 H, OCOCH$_2$CH), 3.98–3.40 (m, 5 H), 3.77 (2 s, in each case 3 H, OMe), 3.16–2.86 (m, 4 H), 2.58 (t, J=7.0 Hz, 1 H, CHCN), 2.38 (t, 1 H, CHCN), 1.80–1.20 (m, 6 H), 1.20, 1.18, 1.17, 1.16, 1.15, 1.13, 1.08, 1.06 (8 s, 12 H, NMe). $^{31}$P-NMR (300 MHz, CDCl$_3$): 149.5, 149.0 (2 s)

Example 4

Synthesis of a p-RNA oligo of the sequence 4'-indole linker-A8–2' using benzimidazolium triflate as a coupling reagent 108 mg of indole linker phosphoramidite and 244 mg of A phosphoramidite are weighed into a synthesizer vial and left in a high vacuum for 3 h in a desiccator over KOH together with the column packed with 28.1 mg of CPG support, loaded with A unit. The phosphoramidites are dissolved in 1 ml (indole linker) or 2.5 ml (A phosphoramidite) of acetonitrile and a few beads of the molecular sieve are added and left closed in the desiccator over KOH.

200 mg of iodine are dissolved in 50 ml of acetonitrile with vigorous stirring. After everything has dissolved (visual control), 23 ml of water and 4.6 ml of sym-collidine are added and the solution is thoroughly mixed once. For detritylation, a 6% strength solution of dichloroacetic acid in dichloromethane is employed. The capping reagent (acetic anhydride+base) is purchased and used as customary for oligonucleotide synthesis.

Benzimidazolium triflate is recrystallized from hot acetonitrile and dried. Using the almost colourless crystals, a 0.1 M solution in anhydrous acetonitrile is prepared as a coupling reagent. During the synthesis, this solution always remains clear and no blockages in the synthesizer tubing occur. Modified DNA coupling cycle in the Eppendorf Ecosyn 300+(DMT on):

| Detritylierung | 7 minutes |
| Coupling | 1 hour |
| Capping | 1.5 minutes |
| Oxidation | 1 minute. |

20 mg of tetrakis(triphenylphosphine)palladium is dissolved in 1.5 ml of dichloromethane, 20 mg of diethylammonium hydrogencarbonate, 20 mg of triphenylphosphine and the glass support carrying the oligonucleotide are added, tightly sealed (Parafilm) and the vial is agitated for 5 h at RT. The glass support is then filtered off with suction by means of an analytical suction filter, and washed with dichloromethane, with acetone and with water.

The support is suspended using aqueous 0.1 molar sodium diethyldithiocarbamate solution and left at RT. for 45 min. It is filtered off with suction, and washed with water, acetone, ethanol and dichloromethane. The support is suspended in 1.5 ml of 24% strength hydrazine hydrate solution, shaken for 24–36 h at 4° C. and diluted to 7 ml with 0.1 molar triethylammonium hydrogencarbonate buffer (TEAB buffer). It was washed until hydrazine-free by means of a Waters Sep-Pak cartridge. It is treated with 5 ml of an 80% strength formic acid solution, and concentrated to dryness after 30 min. The residue is taken up in 10 ml of water, extracted with dichloromethane, and the aqueous phase is concentrated and then HPL chromatographed (tR=33 min, gradient of acetonitrile in 0.1M triethylammonium acetate buffer). Customary desalting (Waters Sep-Pak cartridge) yields the oligonucleotide. Yield: 17.6 OD. Substance identity proved by ESI mass spectroscopy: M(calc.)=3082 D, $(M+2H)^{2+}$(found)=1541.9 D.

Example 5

Preparation of Conjugates

1. Sequential Process

A p-RNA oligomer of the sequence As, i.e. an octamer, is first prepared on the Eppendorf Ecosyn D 300+ as described in Example 2 and the following reagents are then exchanged: 6% strength dichloroacetic acid for 2% strength trichloroacetic acid, iodine in collidine for iodine in pyridine, benzimidazolium triflate solution for tetrazole solution. After changing the synthesis programme, a DNA oligomer of the sequence GATTC is further synthesized according to known methods (M. J. Gait, Oligonucleotide Synthesis, IRI Press, Oxford, UK 1984). The deallylation, hydrazinolysis, HPL chromatography and desalting is carried out as described for the p-RNA oligomer (see above) and yields the desired conjugate.

2. Convergent Process

As described in Example 2, a p-RNA oligomer having the sequence 4'-indole linker-$A_8$-2' is prepared, purified, and iodoacetylated. A DNA oligomer of the sequence GATTC-thiol linker is synthesized according to known methods (M. J. Gait, Oligonucleotide Synthesis, IRL Press, Oxford, UK 1984) and purified (3'-thiol linker from Glen Research: No. 20–2933). On allowing the two fragments to stand (T. Zhu et al., Bioconjug. Chem. 1994, 5, 312) in buffered solution, the conjugate results, which is finally purified by means of HPLC.

Example 6

Synthesis of a p-RNA Oligonucleotide Comprising a Linker with a Linker of the Formula 4' AGGCAIndT 2'

1.1 Solid-phase Synthesis of the Oligonucleotide

A, G, C, T represents the nucleobases adenine, guanine, cytosine and thymine and Ind is aminoethylindole (indole $CH_2$—$CH_2$—$NH_2$) as a linker in the form of a nucleobase.

The fully automatic solid-phase synthesis was carried out using 15 µmol in each case. One synthesis cycle consists of the following steps:

(a) Detritylation: 5 minutes with 6% DCA (dichloroacetic acid) in $CH_2Cl_2$ (79 ml).

(b) Washing with $CH_2Cl_2$ (20 ml), acetonitrile (20 ml) and then flushing with argon;

(c) Coupling: washing of the resin with the activator (0.5 M pyridine•HCl in $CH_2Cl_2$ (0.2 ml) and then 30 minutes' treatment with activator (0.76 ml) and phosphoramidite of the corresponding nucleobase (0.76 ml: 8 eq; 0.1 M in acetonitrile) in the ratio 1/1;

(d) Capping: 2 minutes' treatment with 50% Cap A (10.5 ml) and 50% Cap B (10.5 ml) from PerSeptive Biosystems, Inc., Texas, USA (Cap A: THF, lutidine, acetic anhydride; Cap B: 1-methylimidazole, THF, pyridine);

(e) Oxidation: 1 minute's treatment with 120 ml of iodine solution (400 mg of iodine in 100 ml of acetonitrile, 46 ml of $H_2O$ and 9.2 ml of sym-collidine); and (f) Washing with acetonitrile (22 ml).

To facilitate the subsequent HPLC purification of the oligonucleotides, the last DMT (dimethoxytrityl) group was not cleaved. To detect the last coupling with the modified phorphoramidites, after the synthesis a trityl cation absorption in UV (503 nm) was carried out with 1% of the resin.

1.2 Work-up of the Oligonucleotide:

The allyl ether protective groups were removed with a solution of tetrakis(triphenylphosphine)palladium (272 mg), triphenylphosphine (272 mg) and diethylammonium hydrogencarbonate in $CH_2Cl_2$ (15 ml) after 5 hours at RT. The glass supports were then washed with $CH_2Cl_2$ (30 ml), acetone (30 ml) and water (30 ml). In order to remove palladium complex residues, the resin was rinsed with an aqueous 0.1 M sodium diethyldithiocarbamate hydrate solution. The abovementioned washing operation was carried out once more in a reverse order. The resin was then dried in a high vacuum for 10 minutes. The removal step from the glass support with simultaneous debenzoylation was carried out in 24% hydrazine hydrate solution (6 ml) at 4° C. after HPLC checking on RP 18 (18–25 hours), the oligonucleotide "Trityl ON" was freed from the hydrazine by means of an activated (acetonitrile, 20 ml) Waters Sep-Pak Cartridge. The hydrazine was washed with TEAB, 0.1 M (30 ml). The oligonucleotide was then eluted with acetonitrile/TEAB, 0.1 M (10 ml). The mixture was then purified by means of HPLC for the separation of fragment sequences and the DMT deprotection (30 ml of 80% strength aqueous formic acid) was carried out. Final desalting (by means of Sep-Pak Cartridge, with TEAB buffer 0.1 M/acetonitrile: 1/1) yielded the pure oligonucleotide.

Example 7

Iodoacetylation of p-RNA with N-(iodoacetyloxy) succinimide p-RNA sequence: 4' AGGCAIndT 2' $M_w$=2266.56 g/mol, Prepared According to Example 1

1 eq. of the p-RNA was dissolved (1 ml per 350 nmol) in a 0.1 molar sodium hydrogencarbonate solution (pH 8.4) and treated (40 μl per mg) with a solution of N-(iodoacetyloxy)succinimide in DMSO. The batch was blacked out with aluminium film and it was allowed to stand at room temperature for 30–90 minutes.

The progress of the reaction was monitored by means of analytical HPLC. The standard conditions were:

Buffer A: 0.1 molar triethylammonium acetate buffer in water

Buffer B: 0.1 molar triethylammonium acetate buffer in water:acetonitrile 1:4

Gradient: starting from 10% B to 50% B in 40 minutes

Column material: 10, μM LiChrosphere® 100 RP-18 from Merck Darmstadt GmbH;250×4 mm Retention time of the starting materials: 18.4 minutes Retention time of the products in this case: 23.1 minutes After reaction was complete, the batch was diluted to four times the volume with water. A Waters Sep-Pak Cartridge RP-18 (from 15 OD 2 g of packing) was activated with 2×10 ml of acetonitrile and 2×10 ml of water, the oligonucleotide was applied and allowed to sink in, and the reaction vessel was washed with 2×10 ml of water, rewashed with 3×10 ml of water in order to remove salt and reagent, and eluted first with 5×1 ml of 50:1 water: acetonitrile and then with 1:1 water: acetonitrile. The product eluted in the 1:1 fractions in very good purity. The fractions were concentrated in the cold and in the dark, combined, and concentrated again.

The yields were determined by means of UV absorption spectrometry at 260 nm. Mass spectrometry:

| Sequence: 4' AGGCAInd(CH$_2$CH$_2$NHCOCH$_2$—I)T 2' | |
|---|---|
| calculated mass: | 2434.50 g/mol |
| found mass MH$_2^{2+}$: | 1217.9 g/mol = 2433. |

Example 8

Conjugation of p-RNA to a Defined Peptide (CYSKVG)

The iodoacetylated P-RNA ($M_w$=2434.50 mmol) was dissolved in a buffer system (1000 μl per 114 nmol) and then treated with a solution of the peptide in buffer (2 moleq. of CYSKVG peptide; $M_w$=655.773 g/mol; 228 nmol in 20 μl of buffer). Buffer system : Borax/HCl buffer from Riedel-de Haën, pH 8.0, was mixed in the ratio 1:1 with a 10 millimolar solution of EDTA disodium salt and adjusted to pH 6.3 using HCl . A solution w as obtained by this means which contains 5 mM Na$_2$EDTA.

The batch was left at room temperature in the dark until conversion was complete.

The reaction was monitored by means of HPLC analysis.

The standard conditions were:

Buffer A: 0.1molar triethylammonium acetate buffer in water

Buffer B: 0.1molar triethylammonium acetate buffer in water:acetonitrile 1:4

Gradient: starting from 10% B to 50% B in 40 minutes

Column material: 10 μM LiChrosphere® 100 RP-18 from Merck Darmstadt GmbH; 250×4

Retention time of the starting material: 17.6 minutes

Retention time of the product: 15.5 minutes

After reaction was complete the batch was purified directly by means of RP-HPLC. (Standard conditions see above).

The fractions were concentrated in the cold and in the dark, combined and concentrated again. The residue was taken up in water and desalted. A Waters Sep-Pak Cartridge RP-18 (from 15 OD 2 g of packing) was activated with 2×10 ml of acetonitrile and 2×10 ml of water, the oligo was applied and allowed to sink in, and the reaction vessel was washed with 2×10 ml of water, rewashed with 3×10 ml of water in order to remove the salt, and eluted with water: acetonitrile 1:1. The product fractions were concentrated, combined, and concentrated again.

The yields were determined by means of UV absorption spectrometry at 260 nm. They reached 70–95% of theory.

Mass Spectrometry

| Sequence: 4' AGGCAInd(CH$_2$CH$_2$NHCOCH$_2$—CYSKVG)T 2' | |
|---|---|
| calculated mass MH$_2^{2+}$: | 2962.36 g/mol |
| found mass MH$_2^{2+}$: | 1482.0 g/mol. |

Example 9

Conjugation of p-RNA to a Peptide Library

The iodoacetylated p-RNA ($M_w$=2434.50 g/mol) was dissolved (1300 μl per 832 nmol) in a buffer system and then treated in buffer (8 moleq.; mean molecular mass $M_m$=677.82 g/mol; 4.5 mg=6.66 μmol in 200 pl of buffer) with a solution of the peptide library (CKR—XX—OH; X=Arg, Asn, Glu, His, Leu, Lys, Phe, Ser, Trp, Tyr).

Buffer system : Borax/HCl buffer from Riedel-de Haen, pH 8.0, was mixed in the ratio 1:1 with a 10 millimolar solution of EDTA disodium salt in water and adjusted to pH 6.6 using HCl. A solution was obtained by this means which contained 5 mM Na$_2$EDTA.

The batch was left at room temperature in the dark until conversion was complete.

The reaction was monitored by means of HPLC analysis. In this case, the starting material had disappeared after 70 hours.

The standard conditions of the analytical HPLC are:
Buffer A: 0.1 molar triethylammonium acetate buffer in water
Buffer B: 0.1 molar triethylammonium acetate buffer in water:acetonitrile 1:4
Gradient: starting from 10% B to 50% B in 40 minutes
Column material:10 µM LiChrosphere® 100 RP-18 from Merck; 250×4
Retention time of the starting material: 18.8 minutes
Retention time of the product: several peaks from 13.9–36.2 minutes After reaction was complete, the batch was diluted to four times the volume using water. A Waters Sep-Pak Cartridge RP-18 (from 15 OD 2 g of packing) was activated with 3×10 ml of acetonitrile and 3×10 ml of water, the oligonucleotide was applied and allowed to sink in, the reaction vessel was rewashed with 2×10 ml of water, and the cartridge was washed with 3×10 ml of water in order to remove salt and excess peptide, and eluted with 1:1 water : acetonitrile until product no longer eluted by UV spectroscopy. The fractions were concentrated in the cold and in the dark, combined, and concentrated again.

What is claimed is:

1. A process for the preparation of a linker according to formula (III),

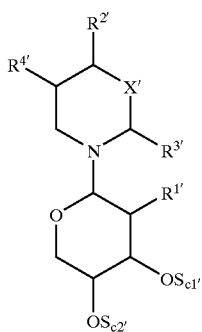

(III)

wherein $R^{4'}$ is $(C_nH_{2n})NR^{10'}R^{11'}$, wherein $R^{10'}R^{11'}$ together form the formula (V),

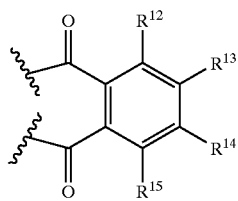

(V)

wherein $R^{12}$, $R^{13}$, $R^{14}$, and $R^{15}$ are independently selected from the group consisting of H, $C_nH_{2n+1}$, $C_nH_{2n-1}$, and $OR^7$, where $R^7$ is equal to H, $C_nH_{2n+1}$ or $C_nH_{2n-1}$, —C(O)$R^8$ where $R^8$ is equal to a linear or branched, optionally substituted alkyl or aryl radical, and where n is equal to an integer from 1–12;
wherein $R^{1'}$ is selected from the group consisting of H, OH, phosphoramidite, Br, and Cl;
wherein $R^{2'}$ and $R^{3'}$ are independently selected from the group consisting of H, an allyloxy radical, and $(C_nH_{2n})NR^{10'}R^{11'}$, wherein $R^{10'}R^{11'}$ have the above-mentioned meaning,
wherein X' in each case is =N—, =C($R^{9'}$)— or —N($R^{9''}$)—, where $R^{9'}$ and $R^{9''}$ are independently selected from the group consisting of H, $C_nH_{2n+1}$, and $(C_nH_{2n})NR^{10'}R^{11'}$, wherein $R^{10'}R^{11'}$ have the above-mentioned meaning, and
wherein $S_{c1}'$ and $S_{c2}'$ are independently selected from the group consisting of an acyl group, trityl group, allyloxycarbonyl group, phosphoester(III), phosphoester(V), thiophosphate(V), phosphonate, and phosphoramidite, the method comprising
(a) reacting a compound of the formula (III) with an azide, wherein $R^{4'}$ is equal to $(C_nH_{2n})OS_{c3}$ or $(C_nH_{2n})$Hal, n is equal to an integer from 1–12, $S_{c3}$ is a branched or unbranched, optionally substituted alkyl, aryl, or acyl group, and Hal is Cl or Br;
(b) reducing the reaction product from (a);
(c) reacting the reaction product from (b) with a phthalimide; and
(d) reacting the reaction product from (c) with a protected pentose.

2. The process according to claim 1 further comprising phosphitylating the 4'-protected pentopyranosyl nucleoside or bonding the 4'-protected pentopyranosyl nucleoside to a solid phase.

3. A process for the preparation of a linker according to formula (I),

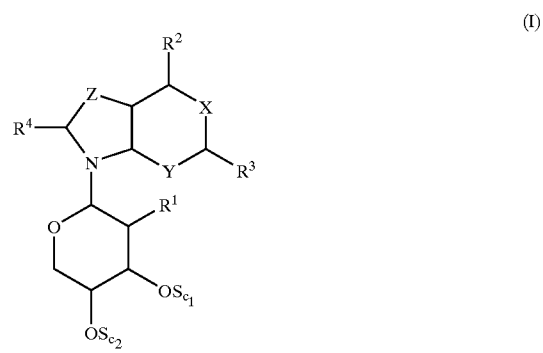

(I)

wherein X and Y are independently selected from the group consisting of =N—, =C($R^9$)—, and —N($R^9$)—, wherein $R^9$ and $R^{9'}$ are independently selected from the group consisting of H and $C_nH_{2n+1}$, and
wherein Z is =C($R^{16}$)—, where $R^{16}$ is equal to $(C_nH_{2n})NR^{10}R^{11}$, and wherein $R^{10}$ and $R^{11}$ are independently selected from H or $C_nH_{2n+1}$, or $R^{10}$ and $R^{11}$ are together form the formula

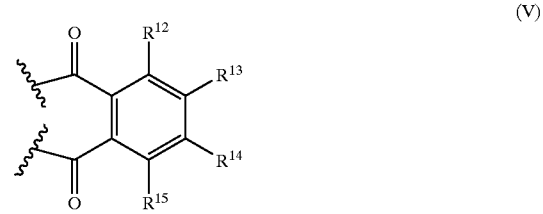

(V)

wherein $R^{12}$, $R^{13}$, $R^{14}$, and $R^{15}$ are independently selected from the group consisting of H, $C_nH_{2n+1}$ $C_nH_{2n-1}$, and $OR^7$, wherein $R^7$ is selected from the group consisting of H, $C_nH_{2n+1}$, $C_nH_{2n-1}$, and —C(O)$R^8$, wherein $R^8$ is equal to a linear or branched, optionally substituted alkyl or aryl radical,
where n is equal to an integer from 1–12, wherein $R^1$ is H, OH, phosphoramidite, Br, or Cl; $R^2$, $R^3$, and $R^4$ are independently H, an allyloxy radical or $(C_nH_{2n})NR^{10}R^{11}$ wherein n, $R^{10}$, and $R^{11}$ are as defined above; and wherein $S_{c1}$ and $S_{s2}$ are independently H or a protective group selected from an acyl group, trityl group, allyloxycarbonyl group, phosphoester (III), phosphoester(V), thiophosphate(V), phosphonate, and phosphoramidite, the process comprising
(a) reacting the corresponding indoline with a pentose to give the nucleoside triol;
(b) protecting the hydroxyl groups of the pentose moiety of the products from (a) with acyl groups; and
(c) oxidizing the product from (b).

4. The process according to claim 3, further comprising phosphitylating the 4'-protected pentopyranosyl nucleoside or bonding the 4'-protected pentopyranosyl nucleoside to a solid phase.

5. A process for the preparation of a pentopyranosyl nucleotide containing nucleic acid comprising
(a) bonding a 3'-, 4'-protected nucleoside of the formula

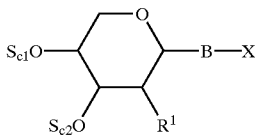

to a solid phase.
wherein $R^1$ is selected from the group consisting of H, OH, phosphoramidite, Br, Cl, and an oligomer;
wherein $S_{c1}$ is selected from the group consisting of H, acyl group, trityl group, allyloxycarbonyl group, phosphoester(III), phosphoester(V), thiophosphate (V), phosphonate, and phosphoramidite;
wherein $S_{c2}$ is selected from the group consisting of H, acyl group, trityl group, allyloxycarbonyl group, phosphoester(III), phosphoester(V), thiophosphate (V), phosphonate, phosphoramidite, and an oligomer;
wherein B is a nucleobase selected from the group consisting of purine, 2,6-diaminopurine, 6-purinethiol, pyridine, pyrimidine, adenine, guanine, isoguanine, 6-thioguanine, xanthine, hypoxanthine, thymine, cytosine, isocytosine, indole, tryptamine, N-phthaloyltryptamine, uracil, caffeine, theobromine, theophylline, benzotriazole, and acridine; and
wherein X is an H or a linker of the formula $-(CH_2)_n-Y$, wherein Y is a protected or deprotected nucleophile or electrophile;
(b) reacting the 3'-, 4'-protected nucleoside bonded to a solid phase according to step (a) with a phosphitylated 3'-, 4'-protected nucleoside of the same formula in step (a), after deprotecting the 4' position of the nucleoside bonded to the solid phase;
(c) oxidizing the coupled product from step (b); and
(d) repeating steps (b) and (c) using identical or different nucleosides or linker nucleosides until the desired nucleic acid is produced, wherein the nucleic acid contains at least one linker of the formula $-(CH_2)_n-Y$.

6. The process according to claim 5, further comprising incorporating pentofuranosyl nucleosides and/or pentopyranosyl nucleosides in step (a) and/or step (b) that do not contain a linker of the formula $-(CH_2)_n-Y$.

7. The process according to claim 5, further comprising removing the protective groups from the nucleic acid, and cleaving the nucleic acid formed from the solid phase.

8. The process according to claim 7, wherein the removal and cleavage is carried out by means of hydrazinolysis.

9. The process according to claim 5, further comprising incorporating a linker of the formula

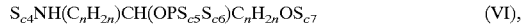

in which $S_{c4}$ and $S_{c7}$ are independently selected from the group consisting of Fmoc and DMT, $S_{c5}$ and $S_{c6}$ are independently selected from the group consisting of an allyloxy and diisopropylamino group, and n is equal to an integer from 1–12, by reacting the phosphite moiety of the linker with the 4' deprotected hydroxyl of the bound nucleoside.

10. A linker of the formula

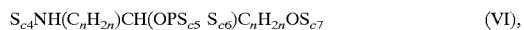

in which $S_{c4}$ and $S_{c7}$ are independently selected from the group consisting of Fmoc and DMT, $S_{c5}$ and $S_{c6}$ are independently a diisopropylamino or allyloxy groups and n is equal to an integer from 1–12.

11. The process according to claim 5, further comprising incorporating a lysine linker of the formula

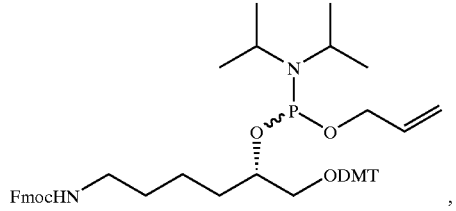

by reacting the phosphite moiety of the linker with the 4' deprotected hydroxyl of the bound nucleoside.

12. The linker of claim 10, comprising the formula

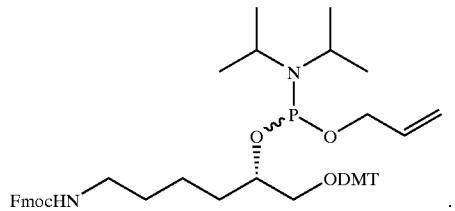

13. A conjugate comprising:
a linker nucleoside of the formula,

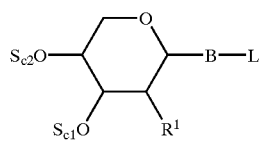

wherein $R^1$ is selected from the group consisting of H, OH, phosphoramidite, Br, Cl, and an oligomer;
wherein $S_{c1}$ is selected from the group consisting of H, acyl group, trityl group, allyloxycarbonyl group, phosphoester(III), phosphoester(V), thiophosphate (V), phosphonate, and phosphoramidite:
wherein $Sc_2$ is selected from the group consisting of H, acyl group, trityl group, allyloxycarbonyl group, phosphoester(III), phosphoester(V), thiophosphate (V), phosphonate, phosphoramidite, and an oligomer;

wherein B is a nucleobase selected from the group consisting of purine, 2,6-diaminopurine, 6-purinethiol, pyridine, pyrimidine, adenine, guanine, isoguanine, 6-thioguanine, xanthine, hypoxanthine, thymine, cytosine, isocytosine, indole, tryptamine, N-phthaloyltryptamine, uracil, caffeine, theobromine, theophylline, benzotriazole, and acridine;

wherein L is a linker of the formula $-(CH_2)_n-Y$, wherein Y is a protected or deprotected nucleophile or electrophile; and a lysine linker, and a biomolecule, wherein the linker nucleoside is covalently attached through a phosphoester bond to the lysine linker, and the biomolecule is covalently attached to the lysine linker through the C6-nitrogen of the linker.

14. The conjugate according to claim 13, wherein the biomolecule is selected from the group consisting of a peptide, peptoid, protein, cell constituent, filament constituent, a nucleic acid, and derivatives thereof.

15. The process of claim 1, for preparation of a linker, wherein $Sc_3$ is a mesylate group.

16. The process of claim 1, further comprising removing the protective groups.

17. The process of claim 3, further comprising removing the hydroxyl protective groups of the pentose moiety of the product from (c).

18. The process of claim 8, wherein the hydrazinolysis is carried out in the presence of salt.

19. A linker nucleoside of the formula:

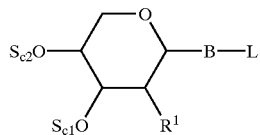

wherein $R^1$ is selected from the group consisting of H, OH, phosphoramidite, Br, Cl, and an oligomer;

wherein $S_{c1}$ is independently selected from the group consisting of: H, acyl group, trityl group, allyloxycarbonyl group, phosphoester(III), phosphoester(V), thiophosphate(V), phosphonate, and phosphoramidite;

wherein $S_{c2}$ is independently selected from the group consisting of: H, acyl group, trityl group, allyloxycarbonyl group, phosphoester(III), phosphoester(V), thiophosphate(V), phosphonate, phosphoramidite, and an oligomer;

wherein B is a nucleobase selected from the group consisting of: indole, tryptamine, and N-phthaloyltryptamine; and wherein L is a linker of the formula $-(CH_2)_n-Y$, wherein Y is a protected or deprotected nucleophile.

20. The linker nucleoside of claim 19, wherein the trityl group is a 4,4'-dimethoxytrityl group.

21. The linker nucleoside of claim 19, wherein $R^1$ and $S_{c2}$ are oligomers.

22. The linker nucleoside of claim 19, wherein Y is $-NR_2$, wherein R is H or a linear or branched, optionally substituted alkyl, aryl, or acyl group.

23. The linker nucleoside of claim 22, wherein $R_2$ is a phthaloyl group.

24. The linker nucleoside of claim 22, wherein Y is $-NHCOCH_2I$.

25. The linker nucleoside of claim 19, wherein the glycosyl moiety is in the D or L configuration.

26. The linker nucleoside of claim 19, wherein B is uracil and L has the formula $-(CH_2)_2NR_2$, and wherein B and L are coupled according to the formula:

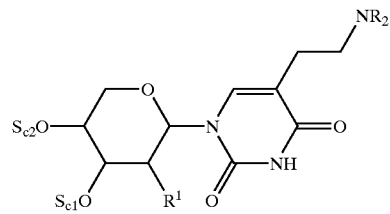

wherein R is a H or a linear or branched, optionally substituted alkyl, aryl, or acyl group.

27. A linker nucleoside of the formula:

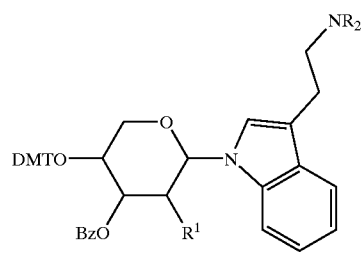

wherein $R^1$ is selected from the group consisting of H, OH, phosphoramidite, Br, Cl, and an oligomer; and wherein Y is a protected nucleoside or electrophile.

28. The linker nucleoside of claim 27, wherein Y has the formula $NR_2$, and wherein R is a H or a linear or branched, optionally substituted alkyl, aryl, or acyl group.

29. The linker nucleoside of claim 28, wherein $R_2$ is a phthaloyl group.

30. The linker nucleoside of claim 19, further comprising a biomolecule coupled to the linker L.

31. The linker nucleoside of claim 30, wherein the biomolecule is selected from a group consisting of peptides, peptoids, proteins, lipids, glycoproteins, filament constituents, viruses, viroids, saccharides, nucleic acids, and their active moieties.

32. The linker nucleoside of claims, wherein the biomolecule is covalently bound to the linker L.

33. The linker nucleoside of claim 19, and wherein B is an indole and L has the formula $-(CH_2)_2NR_2$, wherein the linker nucleoside has the following formula:

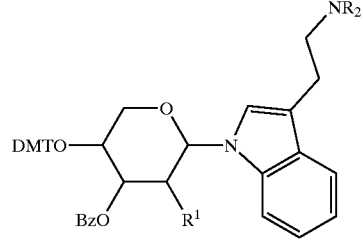

wherein $R^1$ is a phosphoramidite, and wherein R is H or a linear or branched, optionally substituted alkyl, aryl, or acyl group.

34. The linker nucleoside of claim 33, wherein the phosphoramidite includes an allyloxy group and an isopropyl amine.

35. The linker nucleoside of claim 33, wherein $R_2$ is a phthaloyl group.

36. The linker nucleoside of claim 19, and wherein B is a uracil and L has the formula —$(CH_2)_2NR_2$, wherein the linker nucleoside has the following formula:

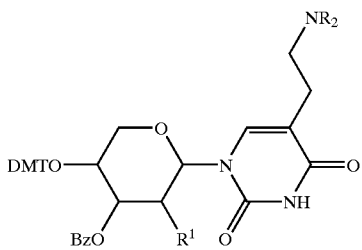

wherein $R^1$ is a phosphoramidite, and wherein R is a H or a linear or branched, optionally substituted alkyl, aryl, or acyl group.

37. The linker nucleoside of claim 36, wherein $R^1$ is an allyloxy group.

38. The linker nucleoside of claim 36, wherein $R_2$ is a phthaloyl group.

39. A linker comprising:

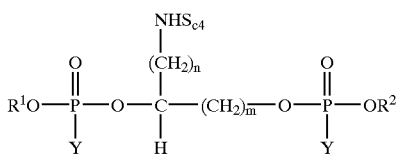

wherein Y is a heteroatom;

wherein $R^1$ and $R^2$ are independently selected from the group of H and an oligomer;

wherein n and m are independently an integer from 1–12, and wherein $S_{c4}$ is a linear or branched, optionally substituted alkyl, aryl, or acyl group.

40. The linker of claim 39, wherein $S_{c4}$ is selected from the group consisting of FMOC and DMT.

41. The linker of claim 39, wherein n=4 and m=1.

42. The linker of claim 39, wherein Y is an oxygen.

43. The linker of claim 39, wherein Y is a sulfur.

44. A linker nucleoside of the formula:

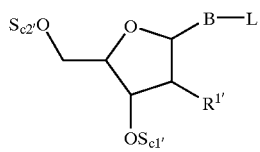

wherein $R^1$ is selected from the group consisting of H, OH, phosphoramidite, Br, Cl, and an oligomer;

wherein $S_{c1'}$ is independently selected from the group consisting of: H, acyl group, trityl group, allyloxycarbonyl group, phosphoester(III), phosphoester(V), thiophosphate(V), phosphonate, and phosphoramidite;

wherein $S_{c2'}$ is independently selected from the group consisting of: H, acyl group, trityl group, allyloxycarbonyl group, phosphoester(III), phosphoester(V), thiophosphate(V), phosphonate, phosphoramidite, and an oligomer;

wherein B is a nucleobase selected from the group consisting of indole, tryptamine, and N-phthaloyltryptamine; and wherein L is a linker of the formula —$(CH_2)_n$—Y, wherein Y is a protected or deprotected nucleophile.

45. The linker nucleoside of claim 44, wherein the trityl group is a 4,4'-dimethoxytrityl group.

46. The linker nucleoside of claim 44, wherein the glycosyl moiety is in the D or L configuration.

47. The linker nucleoside of claim 44, wherein Y is —$NR_2$, wherein R is a H or a linear or branched, optionally substituted alkyl, aryl, or acyl group.

48. The linker nucleoside of claim 47 wherein Y is —$NHCOCH_2I$.

49. The linker nucleoside of claim 44, further comprising a biomolecule coupled to the linker L.

50. The linker nucleoside of claim 49, wherein the biomolecule is selected from a group consisting of peptides, peptoids, proteins, lipids, glycoproteins, filament constituents, viruses, viroids, saccharides, nucleic acids, and their active moieties.

51. The linker nucleoside of claim 49, wherein the biomolecule is covalently bound to the linker L.

52. The process of claim 1, wherein the trityl group is a 4,4'-dimethoxytrityl group.

53. The process of claim 3, wherein the trityl group is a 4,4'-dimethoxytrityl group.

54. The conjugate of claim 13, wherein the trityl group is a 4,4'-dimethoxytrityl group.

* * * * *

UNITED STATES PATENT AND TRADEMARK OFFICE
CERTIFICATE OF CORRECTION

PATENT NO. : 6,699,978 B1
DATED : March 2, 2004
INVENTOR(S) : Miculka et al.

It is certified that error appears in the above-identified patent and that said Letters Patent is hereby corrected as shown below:

<u>Title page,</u>
Item [56], References Cited, U.S. PATENT DOCUMENTS, insert:
-- 4,719,289 A    1/1998    Kolar et al.
   5,849,482 A    12/1998   Meyer et al.
   5,874,553 A    2/1999    Peyman et al. --

FOREIGN PATENT DOCUMENTS, insert:

-- WO    WO95/21184 A2    8/1995
   WO    WO96/12728 A1    5/1996
   WO    WO96/39414 A1    12/1996
   WO    WO96/40711       12/1996
   WO    WO97/00882 A1    1/1997
   EP       0739898 A2    10/1996
   GB       2266182 A     10/1993 --

Signed and Sealed this

Twenty-eighth Day of September, 2004

JON W. DUDAS
*Director of the United States Patent and Trademark Office*